(12) United States Patent
Chu

(10) Patent No.: US 7,598,036 B2
(45) Date of Patent: Oct. 6, 2009

(54) APPARATUS AND METHODS FOR EFFICIENT PROCESSING OF BIOLOGICAL SAMPLES ON SLIDES

(75) Inventor: Wei-Sing Chu, Silver Spring, MD (US)

(73) Assignee: American Registry of Pathology, Washington, DC (US)

( * ) Notice: Subject to any disclaimer, the term of this patent is extended or adjusted under 35 U.S.C. 154(b) by 0 days.

(21) Appl. No.: 11/157,922

(22) Filed: Jun. 22, 2005

(65) Prior Publication Data

US 2005/0238534 A1    Oct. 27, 2005

Related U.S. Application Data

(63) Continuation of application No. 09/869,082, filed as application No. PCT/US99/30519 on Dec. 22, 1999, now abandoned, which is a continuation-in-part of application No. 09/219,443, filed on Dec. 23, 1998, now Pat. No. 6,703,247.

(51) Int. Cl.
    *C12Q 1/68* (2006.01)
    *C12M 1/34* (2006.01)
(52) U.S. Cl. .......................... 435/6; 435/287
(58) Field of Classification Search .............. 436/46; 435/6, 287; 536/22.1
    See application file for complete search history.

(56) References Cited

U.S. PATENT DOCUMENTS

| 4,777,020 | A | | 10/1988 | Brigati |
| 4,798,706 | A | | 1/1989 | Brigati |
| 4,800,159 | A | | 1/1989 | Mullis et al. |
| 4,801,431 | A | | 1/1989 | Cuomo et al. |
| 4,814,269 | A | * | 3/1989 | Karpas ........................ 435/5 |
| 4,849,340 | A | | 7/1989 | Oberhardt |
| 4,975,250 | A | | 12/1990 | Mordecki |
| 4,985,206 | A | | 1/1991 | Bowman et al. |
| 5,002,736 | A | | 3/1991 | Babbitt et al. |
| 5,021,218 | A | | 6/1991 | Davis et al. |
| 5,023,187 | A | | 6/1991 | Koebler et al. |
| 5,192,503 | A | | 3/1993 | McGrath et al. |
| 5,273,905 | A | * | 12/1993 | Muller et al. ............ 435/286.5 |
| 5,346,672 | A | | 9/1994 | Stapleton et al. |
| 5,364,760 | A | | 11/1994 | Chu et al. |
| 5,364,790 | A | | 11/1994 | Atwood et al. |
| 5,415,839 | A | | 5/1995 | Zaun et al. |
| 5,439,649 | A | | 8/1995 | Tseung et al. |
| 5,451,500 | A | | 9/1995 | Stapleton |
| 5,498,392 | A | | 3/1996 | Wilding et al. |
| 5,527,510 | A | | 6/1996 | Atwood et al. |
| 5,538,871 | A | | 7/1996 | Nuovo et al. |
| 5,556,773 | A | | 9/1996 | Yourno |
| 5,658,723 | A | | 8/1997 | Oberhardt |
| 5,955,377 | A | * | 9/1999 | Maul et al. .................. 436/518 |
| 5,958,341 | A | | 9/1999 | Chu |
| 5,958,760 | A | | 9/1999 | Freeman |
| 6,010,910 | A | | 1/2000 | Radcliffe et al. |
| 6,087,102 | A | * | 7/2000 | Chenchik et al. ............... 435/6 |
| 6,143,496 | A | | 11/2000 | Brown et al. |
| 6,181,811 | B1 | | 1/2001 | Kuan et al. |
| 6,465,178 | B2 | * | 10/2002 | Chappa et al. ................. 435/6 |

FOREIGN PATENT DOCUMENTS

WO    WO 97/07241 A1    2/1997

OTHER PUBLICATIONS

Brigati, D.J., et al., "Immunocytochemistry is Automated: Development of A Robotic Workstation Based Upon the Capillary Action Principle", *J. of Histotechnology* Sep. 1988; 11(3):165-183.

Chiu, K-P, et al., "Intracellular Amplification of Proviral DNA in Tissue Sections Using the Polymerase Chain Reaction", *J. of Histochemistry and Cytochemistry* 1992; 40(3):333-341.

Embretson, J., et al., "Analysis of human immunodeficiency virus-infected tissues by amplification and in situ hybridization reveals latent and permissive infections at single-cell resolution", *Proc. Natl. Acad. Sci. USA* Jan. 1993; 90:357-361.

Komminoth, P., et al., "In Situ Polymerase Chain Reaction Detection of Viral DNA, Single-Copy Genes, and Gene Rearrangements in Cell Suspensions and Cytospins", *Diagn. Mol. Pathol.* 1992; 1(2):85-97.

Man, Y-G, et al., "Detailed RT-ISPCR Protocol for Preserving Morphology and Confining PCR Products in Routinely Processed Paraffin Sections", *Cell Vision* 1996; 3(5):389-396.

McGrath, C.M., et al., "Influence of Surface:Volume Ratio of Reaction Chambers on Stoichiometry of Antibody-Based Reactions In Situ", *Cell Vision* 1995; 2:165-169.

(Continued)

*Primary Examiner*—Suryaprabha Chunduru
(74) *Attorney, Agent, or Firm*—Rothwell, Figg, Ernst & Manbeck p.c.

(57) ABSTRACT

Microscope slides which are useful for manually or automatically processing biological samples are described. External controls may be placed directly on the microscope slide in conjunction with a biological sample to be assayed. The external controls can also be conveniently placed on a membrane which can be affixed to the slide.

13 Claims, 12 Drawing Sheets

OTHER PUBLICATIONS

Mies, C., "A Simple, Rapid Method for Isolating RNA from Paraffin-embedded Tissues for Reverse Transcription-Polymerase Chain Reaction (RT-PCR)", *J. of Histochemistry and Cytochemistry* 1994; 42(6):811-813.

Nuovo, G.J., "In Situ Detection of PCR-amplified DNA and cDNA: A Review", *J. of Histotechnology* Sep. 1994; 17(3):235-246.

Nuovo, G.J., et al., "An Improved Technique for the In Situ Detection of DNA After Polymerase Chain Reaction Amplification", *Am. J. Pathol.* Dec. 1991; 139(6):1239-1244.

Price, T.M. and O'Brien, S.N., "Determination of Estrogen Receptor Messenger Ribonucleic Acid (mRNA) and Cytochrome P450 Aromatase mRNA Levels in Adipocytes and Adipose Stromal Cells by Competitive Polymerase Chain Reaction Amplification", *J. Clin. Endocrinol. Metab.* 1993; 77(4):1041-1045.

Shibata, D., et al., "Specific Genetic Analysis of Microscopic Tissue After Selective Ultraviolet Radiation Fractionation and the Polymerase Chain Reaction", *Am. J. Pathol.* Sep. 1992; 141(3):539-543.

Staskus, K.A., et al., "In situ amplification of visna virus DNA in tissue sections reveals a reservoir of latently infected cells", *Microbial Pathogenesis* 1991; 11:67-76.

Turbett, G.R., et al., "Single-Tube Protocol for the Extraction of DNA and RNA from Paraffin-Embedded Tissues Using a Starch-Based Adhesive", *BioTechniques* 1996; 20:846-850, 852-3.

MJ Research, Inc. (1996). Two (2) pages of information from MJ Research, Inc. concerning "Frame-Seal Incubation Chambers for Sealing Reactions on Slides".

PGC Scientifics Molecular Biology Catalog (1996). Three (3) pages from this catalog (pp. 73, 82 and 83).

Description of the Shandon Lipshaw Cadenza® Automated Immunostainer, pp. 1-8, 1989.

\* cited by examiner

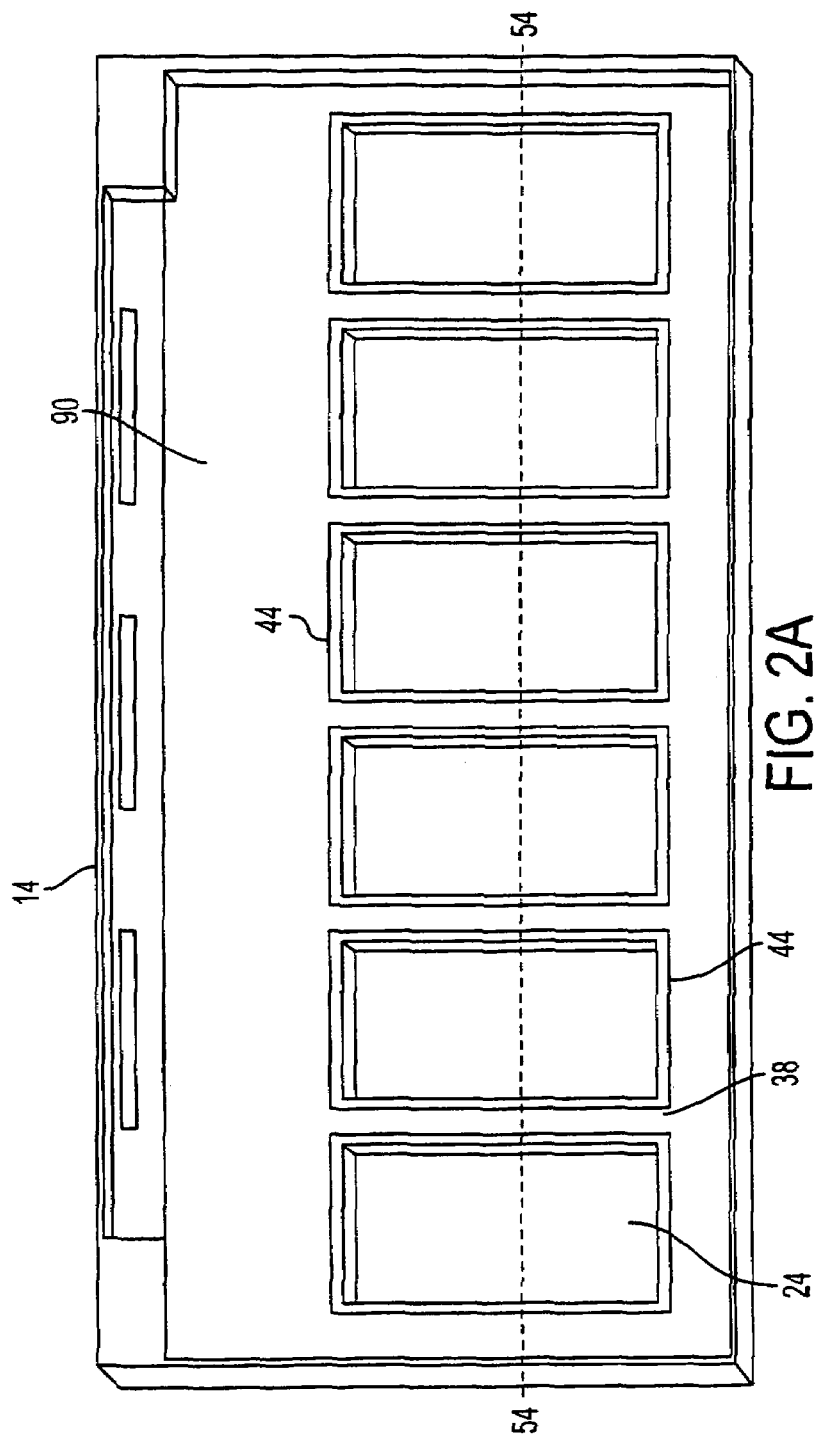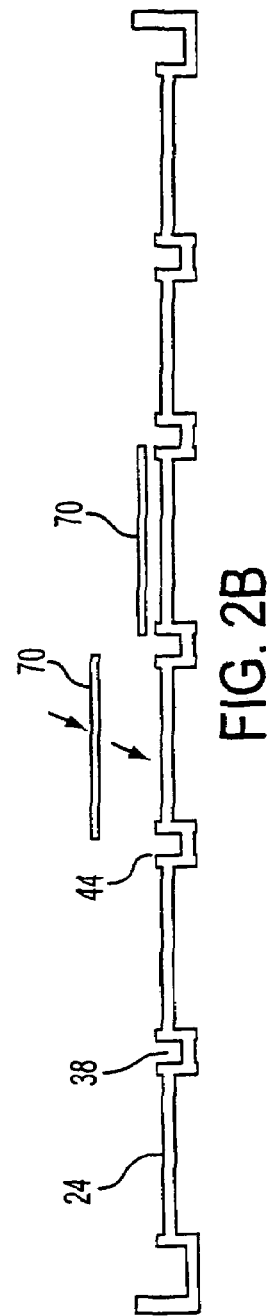

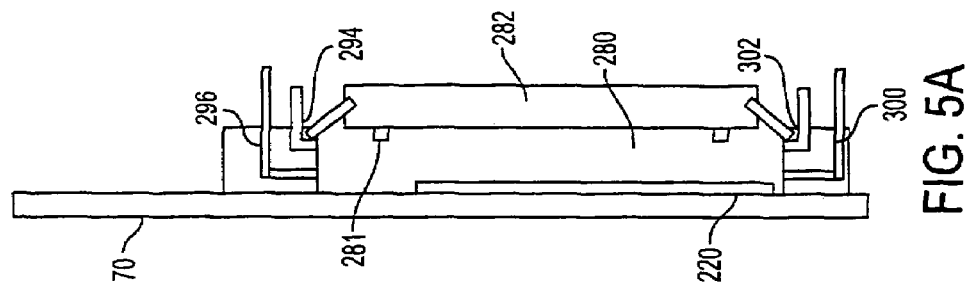
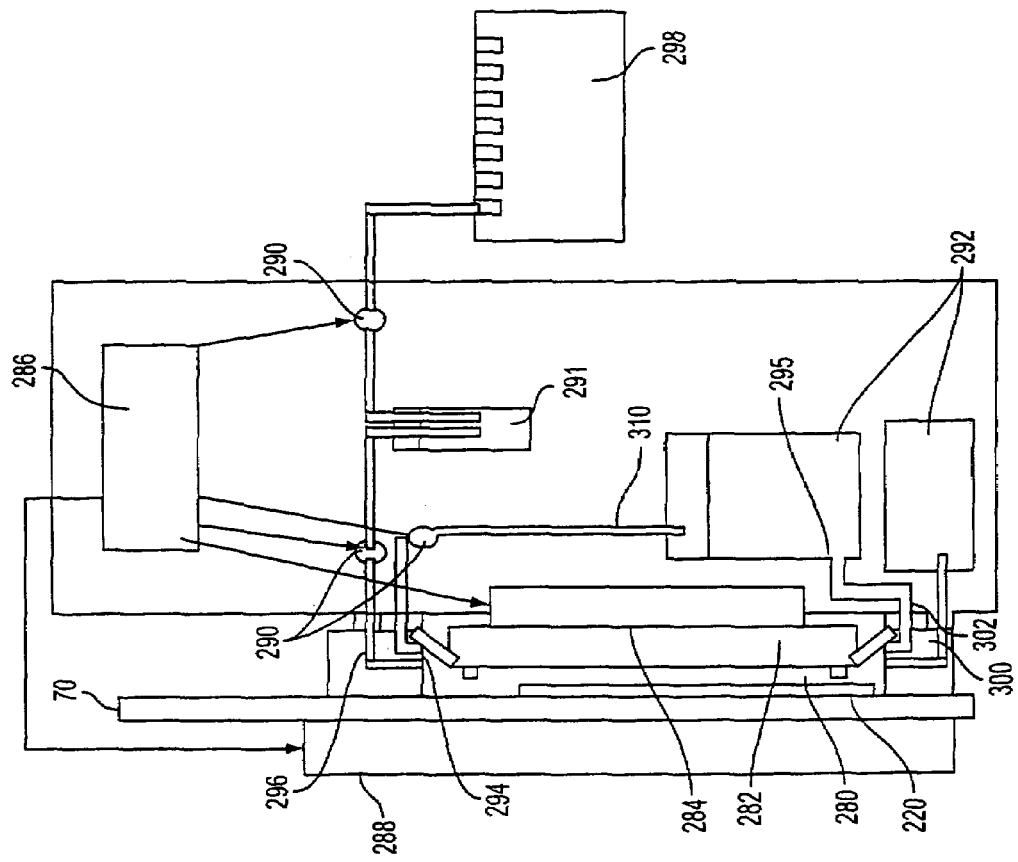

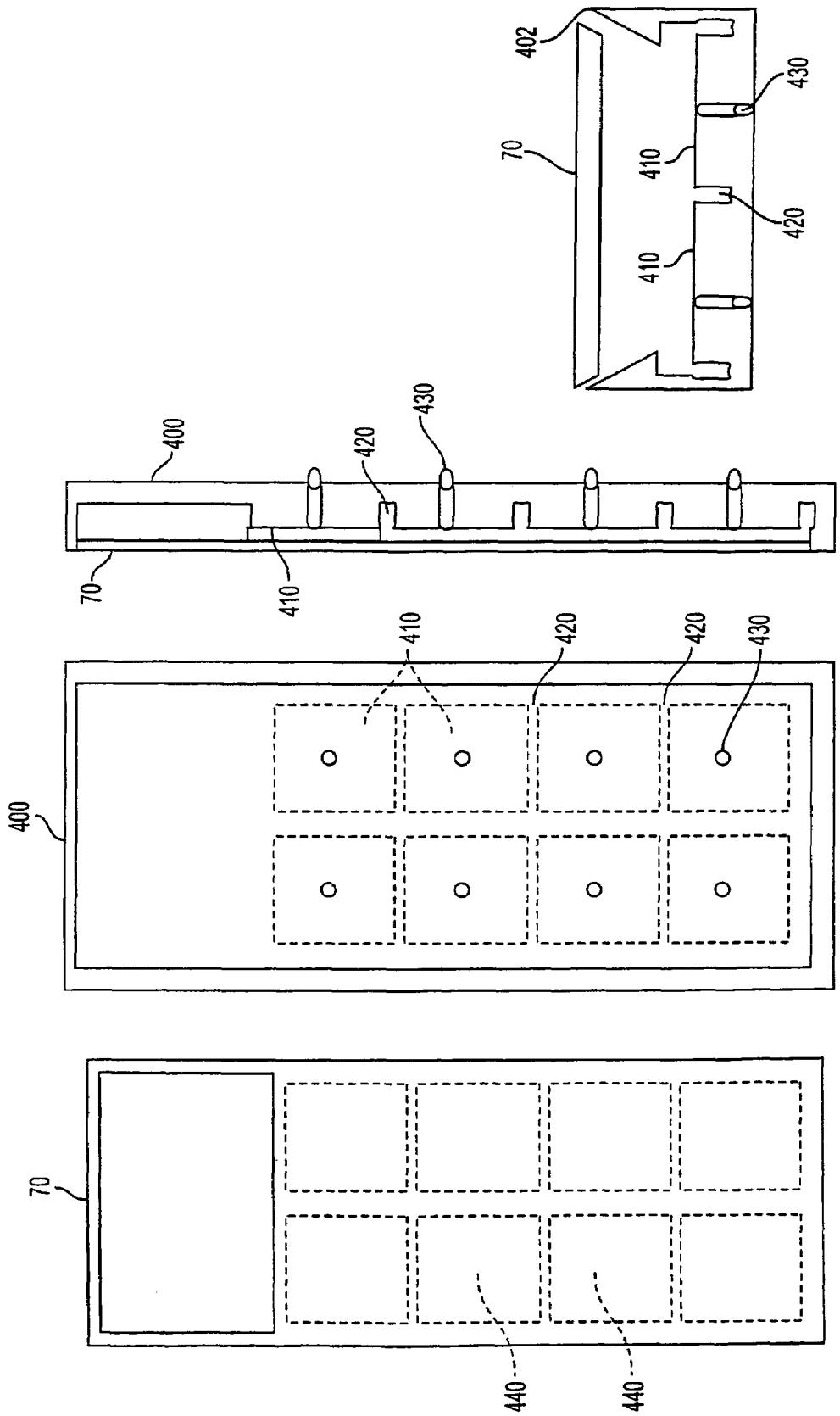

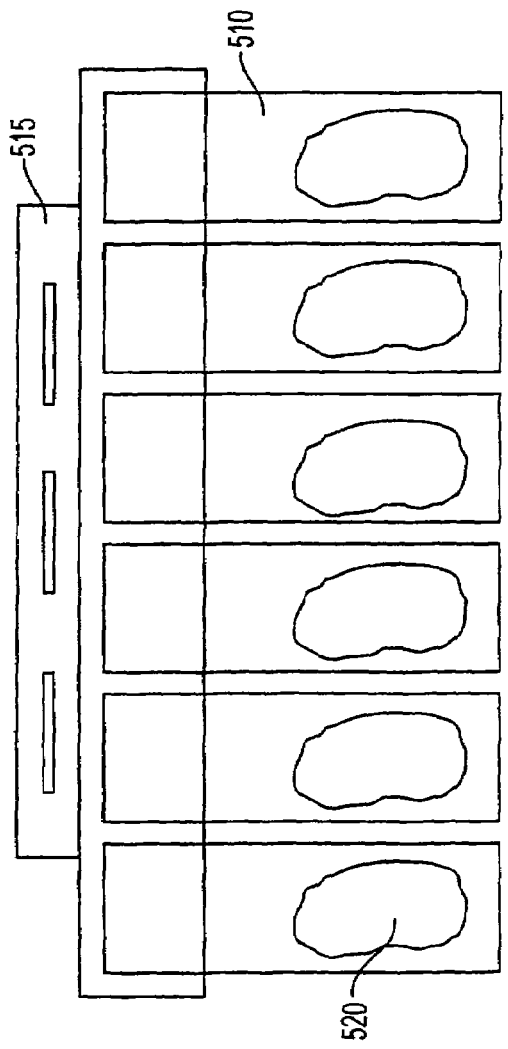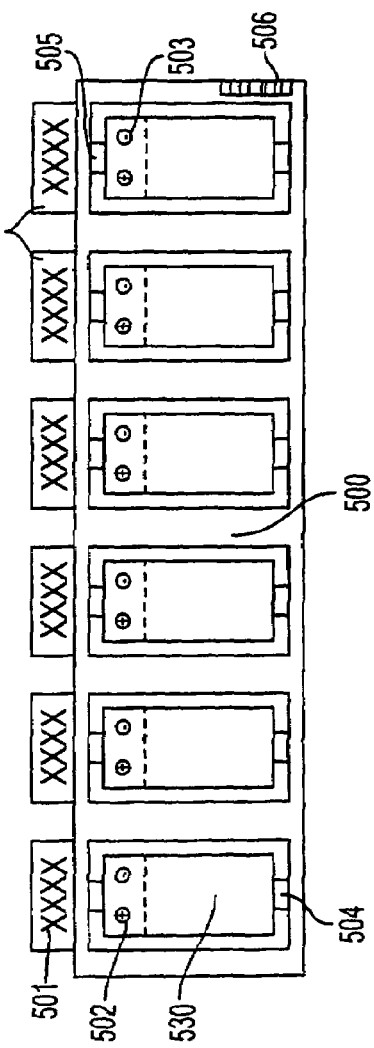
FIG. 7A
FIG. 7B

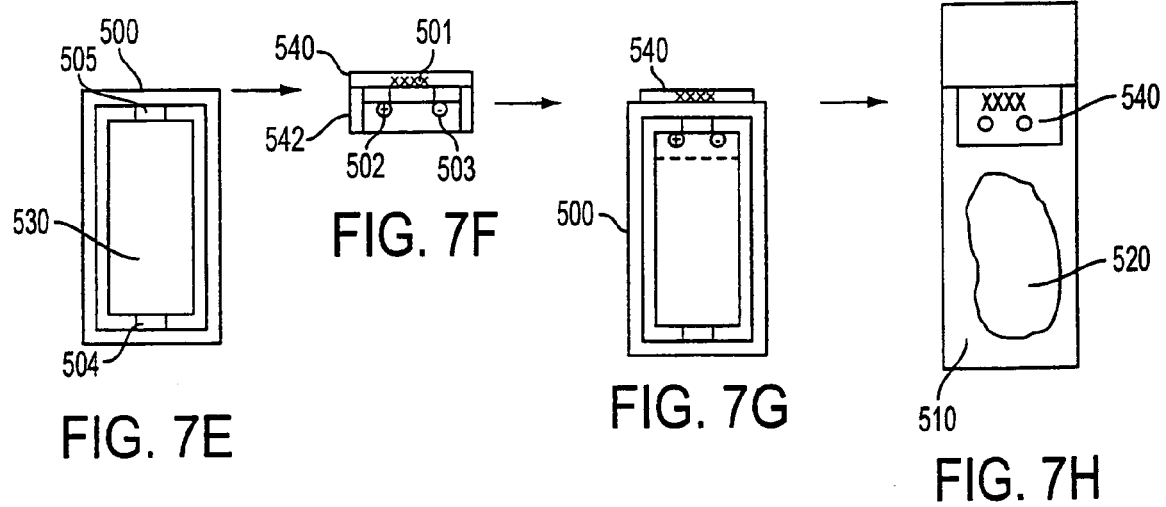

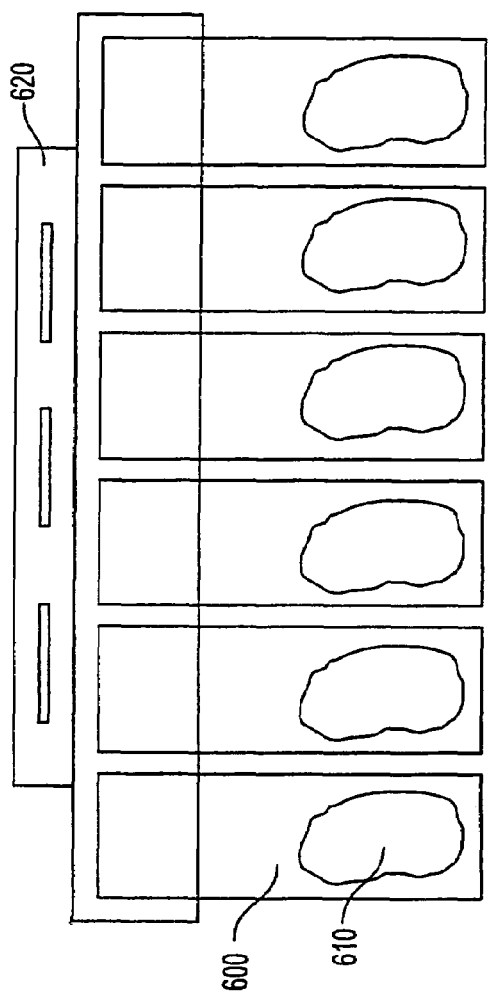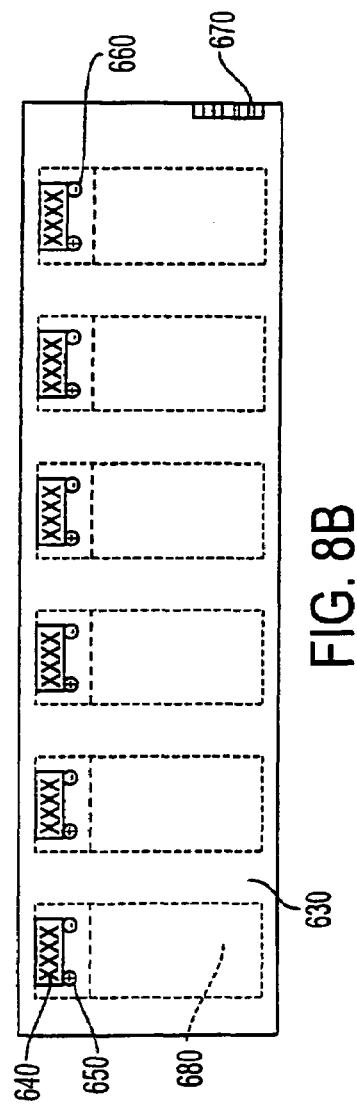

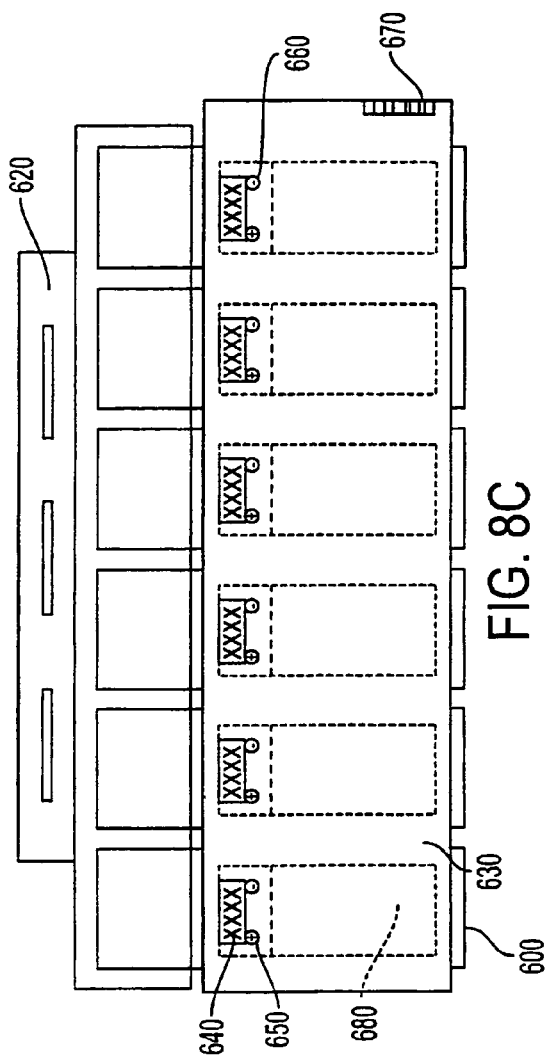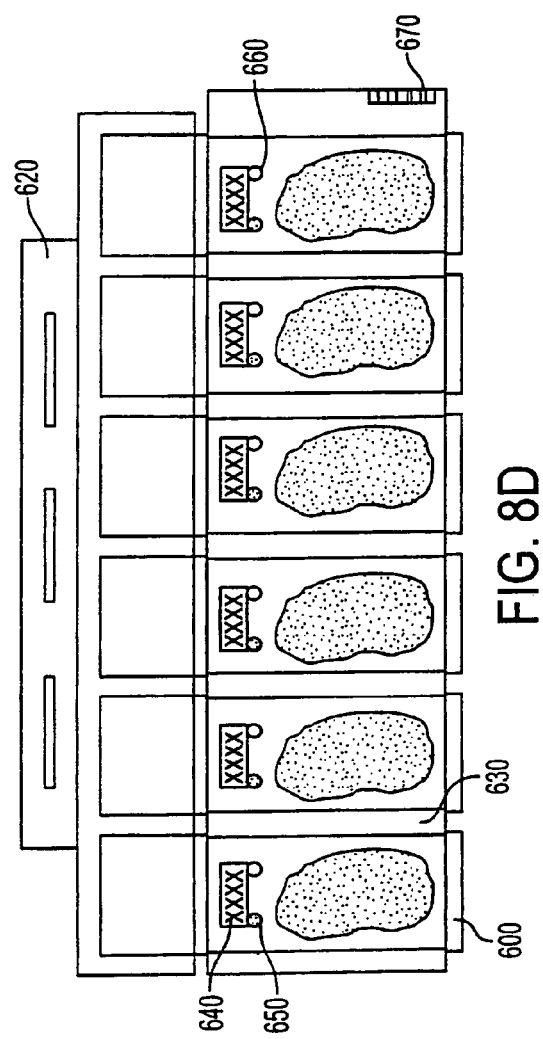

APPARATUS AND METHODS FOR EFFICIENT PROCESSING OF BIOLOGICAL SAMPLES ON SLIDES

CROSS-REFERENCE TO RELATED APPLICATIONS

This application is a continuation of U.S. patent application Ser. No. 09/869,082, filed Sep. 24, 2001 now abandoned, which was filed under 35 U.S.C. § 371 based on PCT/US99/30519, filed 22 Dec. 1999, which is a continuation in part of U.S. Ser. No. 09/219,443, filed 23 Dec. 1998 now U.S. Pat. No. 6,703,247. This application claims priority to both PCT/US99/30519 and to U.S. Ser. No. 09/219,443, as well as U.S. patent application Ser. No. 09/869,082, the contents of which are incorporated herein in their entirety.

BACKGROUND OF THE INVENTION

This invention relates to an apparatus for processing biological samples on slides for a wide variety of purposes. Biological samples are analyzed for many purposes using a variety of different assays. Pathologists often use histochemistry or immunocytochemistry for analyzing biological samples, molecular biologists may perform in situ hybridization or in situ polymerase chain reactions on biological samples, etc. Often the sample to be analyzed will be embedded in paraffin and mounted on a microscope slide.

The assays usually involve the use of antibodies, enzymes and other expensive reagents and it is desirable to keep reagent volume use to a minimum to lower costs. These assays are also quite labor intensive although there are now some automated systems (e.g., the Ventana ESIHC Staining System, the Shandon Lipshaw Cadenza Automated Immunostainer; also see Brigati et al. (1988)). The publications and other materials used herein to illuminate the background of the invention or provide additional details respecting the practice, are incorporated by reference, and for convenience are respectively grouped in the appended List of References. Most automated systems can only perform 40 to 48 slides per run. Fisher automated systems can perform 120 slides per run. Most automated systems which only perform immunocytochemistry do not perform deparaffinizing, histochemistry (such as hematoxylin and eosin staining) and coverslipping steps and these consequently must be done separately by hand which is time and labor intensive. The automated systems perform only a small part of the overall process of preparing and analyzing slides. Steps which are still manually performed prior to the automated portion include sorting of cases and slides, labeling slides, programming the automated equipment, daily antibody and reagent preparation, preparing control tissue which is mounted on slides, and microwave antigen retrieval. Procedures still performed manually after the automated steps are dehydration, coverslipping, slide labeling and sorting of slides and cases. Furthermore, most commercial ready-to-use reagents are not suitable for automated systems which are required to use specially designed reagents. Laboratories which process large numbers of samples are likely to be willing to pay the high cost associated with buying these automated systems as well as the high cost of using the disposable accessories and reagents to perform the assays, but small to intermediate sized laboratories find it more cost effective to continue to process samples manually.

A typical immunocytochemistry assay requires a series of many steps. These include: obtaining a biological sample such as from a biopsy, fixing the sample in formalin, processing the sample overnight, embedding the sample in paraffin, cutting serial sections and mounting on microscope slides and drying. These steps are followed by steps to deparaffinize (treatments in xylene, ethanol and water), and finally the reaction can be preformed on the sample which has been mounted on the slide. Typically a series of solutions including reagents such as enzymes, primary antibody, secondary antibody, detection reagent, chromogen, counterstain, etc. is dropped onto the slide, incubated, and washed off. Finally the sample may be viewed under the microscope. Clearly there are many individual steps involved and each sample on a slide must be processed individually. Besides being very labor intensive, there are drawbacks associated with the commonly used method of simply dropping solutions on top of the mounted sample on the microscope slide. The solution is not restricted simply to the area of the biological sample itself and the solution may be relatively deep rather than being a thin layer. These features require use of extra reagents which are quite expensive. Leaving the solutions open to the air as they sit on the slide also may lead to evaporation if the samples must incubate for a long period of time. Evaporation leads to concentration or drying out of the reagents and high concentrations may lead to increased background levels which are clearly undesirable. If the solutions evaporate totally the assay will fail. Incubating samples in humidity chambers with covers may prevent evaporation problems, but water droplets which condense onto the humidity chamber cover may fall onto the slides and this will ruin the assay.

Improved methods for more rapidly assaying several samples at once, but without the high cost of automated systems, will be welcomed by small to intermediate sized laboratories. Furthermore, methods which will allow use of smaller amounts of reagents and overcome the drawbacks of processing samples on slides open to the atmosphere will be a welcome advance.

SUMMARY OF THE INVENTION

The present invention relates to an apparati and methods for performing assays on biological samples mounted on microscope slides. Use of the apparati and/or methods aid in making assays more rapid and convenient. One aspect of the invention is the use of reagents which are predried in the wells of the tray thereby simply necessitating the addition of water or buffer to the well without having to add the reagents at the time of assay. The well is then covered with a slide with a biological sample premounted on the slide. The different wells of a multiwell tray can be pretreated with different reagents dried in each well. Multistep assays can be performed by moving a slideholder with attached slides from one multiwell tray to the next, with each well of a multiwell tray having the desired reagents predried on it. A variation of this is to employ a multilayer coating of reagents in each well such that the first set of reagents dissolves quickly and acts upon the biological sample, the second layer then dissolves releasing the reagents for the second step, etc., thereby requiring the use of fewer trays, possibly only a single tray.

Another aspect of the invention is to have built in controls on each slide. This is a portion of the slide to which are attached positive and negative controls. These controls allow one to determine whether the assay has worked properly for each individual slide since each slide has its own set of controls and which simultaneously act as labels for each slide.

The invention is also directed to a coverslip with concave wells for holding reagents. The coverslip can be mounted onto a slide so that it will hold reagents for performing analyses but is easily removed to allow washing of the slide. The cover slip can include controls dried onto it for the assay.

Another aspect of the invention is automated processing of biological samples in a reaction chamber in conjunction with a coverslip which has reagents predried onto it and can optionally have control sample prespotted onto it.

BRIEF DESCRIPTION OF THE DRAWINGS

FIGS. 2A-B illustrate a tray 14 and slides 70. FIG. 2A is a front elevational view of tray 14. Wells 24 are separated by troughs 38. Boundaries 44 of wells 24 are flat and are elevated above the interior portion of the wells 24. Trough 90 is contiguous with troughs 38. FIG. 2B is a cross sectional view of tray 14 taken along line 54-54 of FIG. 2A. This view shows wells 24, troughs 38, and well boundaries 44. Slide 70 is shown resting on one well 24.

FIGS. 5A-B illustrate one well of a multiwell tray 330 which is used to automate several steps of the procedure of assaying a biological sample in conjunction with a thermal cycler, pumps and a central processing unit. FIG. 5A shows slide 70 with mounted biological sample 220 placed on a well or reaction chamber 280. Inlets 300 and 302 and outlets 294 and 296 which connect to reaction chamber 280 are illustrated. The portion of tray 330 which forms the bottom of the reaction chamber 280 is shown as 282. Optional stops 281 are shown which prevent the reaction chamber bottom 282 from pressing up against sample 220. The view in FIG. 5A shows the reaction chamber bottom 282 in an "open" mode which causes the reaction chamber 280 to have a large volume. FIG. 5B shows the tray and slide of FIG. 5A in conjunction with other optional equipment. In FIG. 5B the reaction chamber bottom 282 is in a "closed" mode such that reaction chamber 280 encompasses a smaller volume than seen in FIG. 5A. Piston 284 to move reaction chamber bottom 282 is shown. The piston 284 is controlled by central processing unit 286. A thermal cycler 288 is illustrated pressed against slide 70. The thermal cycler can also be controlled by central processing unit 286. Tubing can be attached to the inlets 300 and 302 and to the outlets 294 and 296. Pumps 290 attached to the tubing are shown and pump liquid to or from reservoirs 291 or 292 or to gel 298.

FIGS. 6A-E illustrate a tray used to perform whole chromosome painting of multiple chromosomes on cells on a single slide or which can be used to perform in situ hybridization or FISH on a biological sample. FIG. 6A illustrates an 8 well tray 400 with wells 410. Each well is separated from neighboring wells by troughs 420. Each well 410 has an opening or channel 430 through which liquid can be pipetted. FIG. 6B is a side view of the 8 well tray 400 shown in FIG. 6A. A slide 70 is shown on the tray 400. Four wells 410 are illustrated with three of the wells being empty and one shown filled with liquid. Openings 430 and troughs 420 are also illustrated. FIG. 6C is an end-on view of the slide and tray of FIGS. 6A and 6B. Trough 420 is shown between two wells 410. Openings 430 into the wells 410 are shown. Slide 70 is shown resting above sides of tray 400 showing optional clips 402 to hold slide 70 to tray 400. FIG. 6D is a schematic showing a slide 70 illustrating 8 regions 440 of the slide which will be in contact with each of the 8 wells 410. This is only illustrative, there being no need to actually denote these regions 440 on the slides used in practice. FIG. 6E illustrates one manner of designing built-in controls on slide 70 by showing an enlargement of one region 440. Each region 440 has nucleic acids 442, which hybridize to the probes being used in the assay, placed in an array around the perimeter of region 440. These controls will be in contact with probe during the hybridization.

FIGS. 7A-H illustrate the processing of a biological sample on a slide in conjunction with a coverslip with concave wells.

FIGS. 8A-D illustrate processing of a biological sample on a microscope slide in conjunction with a coverslip.

DETAILED DESCRIPTION OF THE INVENTION

The present invention is an integrated system for processing biological samples on microscope slides in a more rapid and efficient and less costly manner than is typical. Much of the background for this disclosure is shown in U.S. Pat. No. 5,958,341 (W.-S. Chu; issued Sep. 28, 1999) which is incorporated herein by reference. The numbering of parts used in this disclosure, if not shown in a Figure herein, refers to the numbering shown in Figures of U.S. Pat. No. 5,958,341 (W.-S. Chu).

Figure 1:
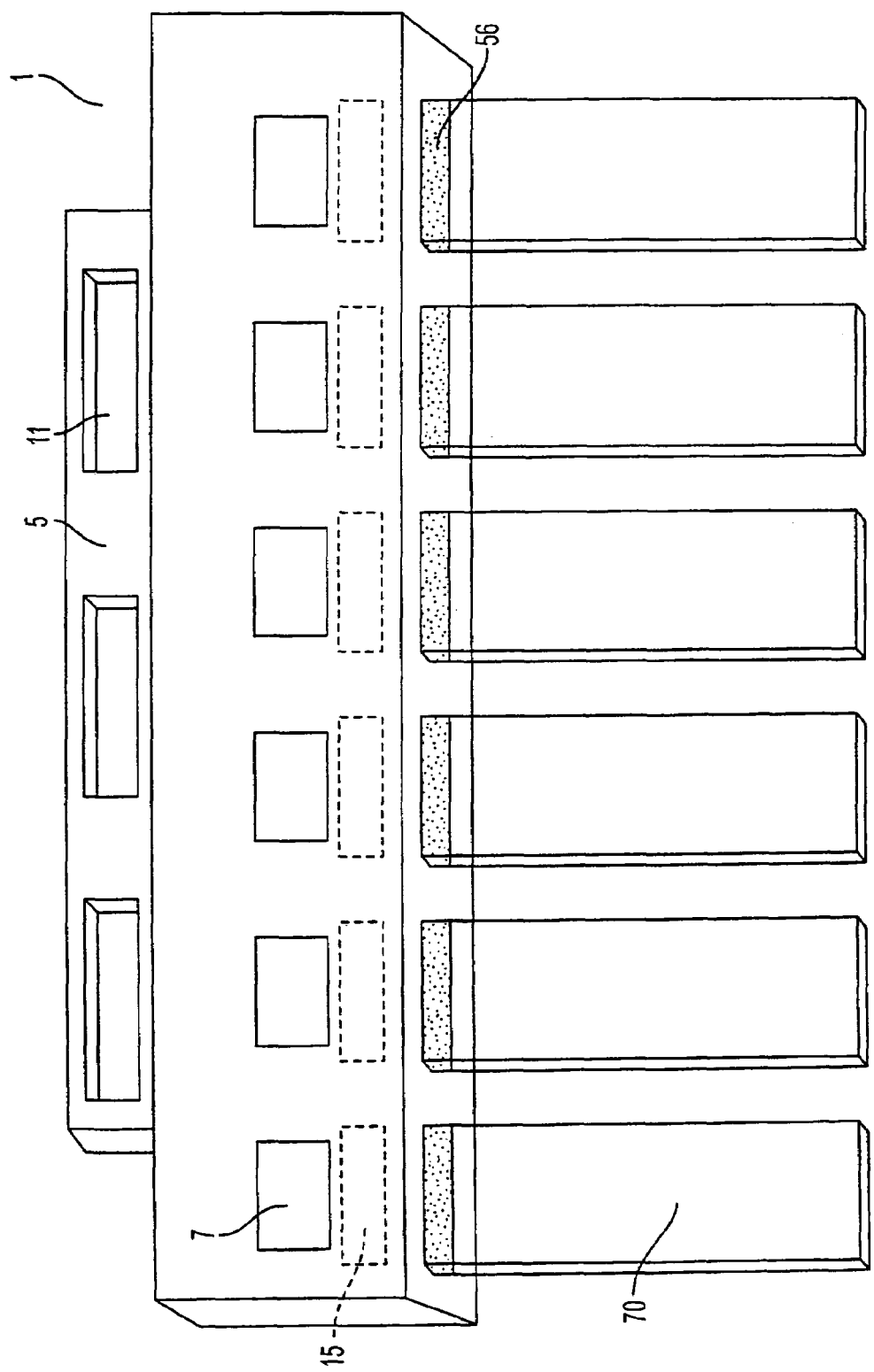
FIG. 1 illustrates a slideholder 1 with slides 70. Slideholder 1 includes a handle 5 with holes 11. Openings 7 in the slideholder allow labels on slides 70 to be seen. Labels may also be attached directly to the slideholder 1 at region 15. Slides 70 are inserted into slots 56 of slideholder 1.

By a biological sample is meant a tissue section, biopsy, cell smear, nucleic acid, protein or peptide, chromosome, bodily fluid or other biological material commonly observed under a microscope. The system as illustrated in FIGS. 1 and 2A-B consists of a slideholder and a tray or a coverslip (see FIGS. 7A-H and 8A-D) for simultaneously holding multiple, preferably up to six, microscope slides to allow for concurrent processing of the multiple slides. The slideholder may be reusable.

Figure 4:
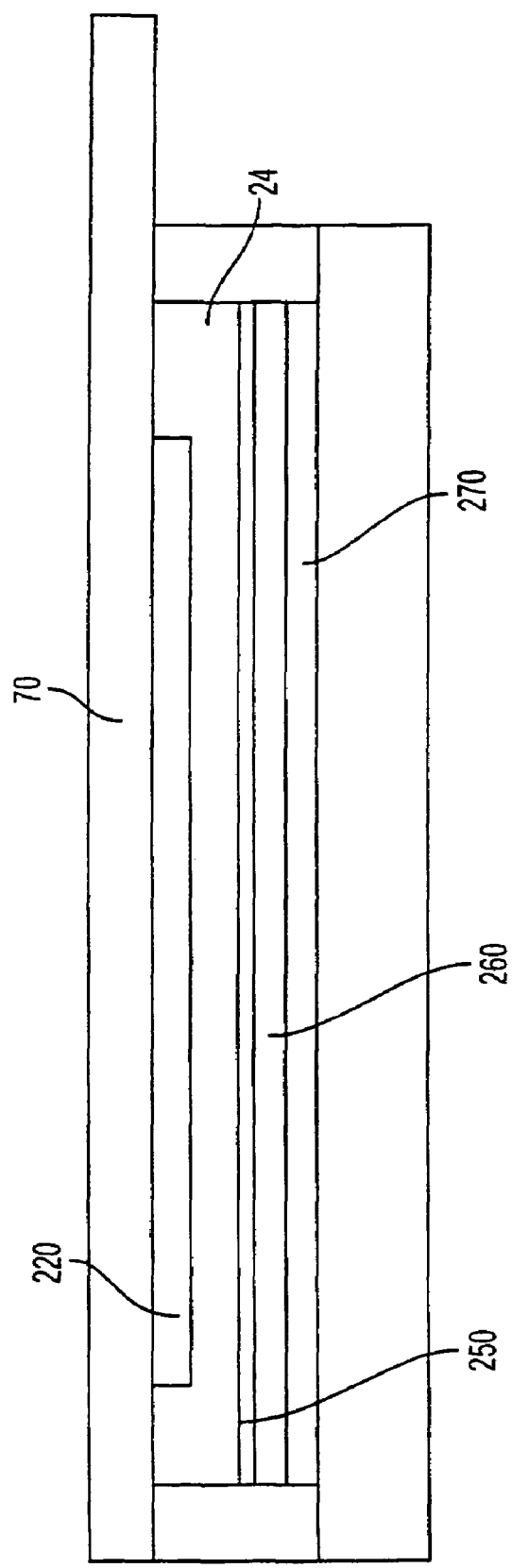
FIG. 4 illustrates a well 24 in which three reagents (indicated as 250, 260, and 270) have been dried and onto which has been placed a slide 70 with mounted biological sample 220. Layers of inert material separating the layers of reagents from each other are not shown.

In practice, a biological sample is mounted onto each of the slides to be analyzed. This often involves steps of fixing a biological sample in formalin, embedding the sample in paraffin, cutting thin, serial sections from the paraffin or from frozen tissue sections and mounting the sections onto the microscope slides. These are dried overnight at room temperature. The mounted biological samples are subjected to some type of assay such as staining. For this the mounted samples must be placed in contact with a series of solutions with washing steps in between each different change of reagent. In the present invention the reagents are measured into or predried in each well 24 in the trays 14. Enough reagent or buffer is added to completely fill the well 24 such that the solution in the well 24 will contact the microscope slide 70 which is to be laid on top of the well 24. There should be no air bubbles present between the solution in the well 24 and the microscope slide 70. By exactly filling the well 24 or by slightly overfilling the well 24 so that there is a slight overflow once the slide 70 is placed on top of the well 24 (surface tension holding the top of the solution in the well 24 prior to a slide 70 being placed onto it) there is no problem with air bubbles forming. Capillary action of the fluid in the well 24 contacting the slide 70 allows for good contact between the biological sample and reagents across the complete well 24 area and helps to seal the well 24. Trays 14 may be designed to include a hook on one edge of a well boundary 44. This is shown in FIGS. 4C and 4F of U.S. Pat. No. 5,958,341 (W.-S. Chu). By pushing all of the slides 70 against the hooks, all of the slides will be held against the well boundaries 44 and this will assure good contact with the reagents within the wells 24.

By placing the slides 70 onto the tray 14 in the above manner, the mounted biological sample is facing down into the well 24 and is not exposed to the atmosphere. This prevents extraneous material from falling into the reagent or onto the biological sample during incubation. Furthermore, the slide 70 covers the well 24 and helps to prevent evaporation of the reagent solution in the well 24 during incubation. Evaporation may lead to very bad background signals. The present invention helps to overcome this problem.

After incubation with each reagent the slideholder 1 and tray 14 are picked up and put into a standard staining dish with 500 milliliters of phosphate buffered saline (PBS) solution. Once in the PBS, the surface tension between the slides 70 and the tray 14 disappears and the slides are very easily removed from the tray. The slides are then put through the appropriate washing steps. It is a simple matter to pick up six slides 70 at once since they are all attached to a single holder 1. A standard staining dish in a laboratory is large enough to accommodate six slides 70 across (as attached to a single slideholder 1) and can contain 20 slideholders 1. Therefore 120 slides 70 may be washed and processed simultaneously.

The above methods are an improvement because they result in an enclosed assay system which helps to prevent contamination. Also, the enclosed system prevents evaporation resulting in a constant volume of reagent being present thereby resulting in a known amount of and constant concentration of reagents. These features lead to better and more consistent results than prior art methods, e.g., those wherein reagents are simply dropped on top of a tissue sample mounted on a slide and which is open to the atmosphere thereby allowing contamination and evaporation.

Another aspect of the invention is to predry reagents in wells 24 of trays 14 thereby requiring simply the immersion of the tray 14 and slides 70 into water or buffer or the pipetting of water or a buffer into the wells 24 at the time of assay. Trays 14 can be prepared which include a series of reagents predried in the wells 24 of a multiwell tray 14, e.g. each well 24 of a multiwell tray 14 can have a different set of reagents dried in the well 24. At the time of assay, slides 70 can have a biological sample from a single patient or from different patients mounted on them and be placed onto a single tray 14 to perform multiple assays at once. Such trays 14 with predried reagents can be prepared ahead of time and stored until the time of use. As currently practiced, assays performed on biological samples are performed by fixing a sample onto a slide and then dropping reagents onto the sample. Such a method cannot take advantage of premeasured, predried reagents which require only the addition of water or buffer. In the invention disclosed here, the reagents can be predried in a well 24 on a tray 14, buffer or water is added to well 24, and a slide 70 with biological sample mounted on it is placed on top of well 24, sample side down. The buffer or water may be added to well 24 via tubing after placing slide 70 on top of well 24. Having slide 70 over well 24 forms a sealed reaction chamber which prevents contamination and evaporation and also ensures uniform distribution of reagents as compared to dropping solution on top of a slide as is generally done in current practice.

Yet another aspect of the invention is to have built-in controls and/or labels on each slide. Known controls are immobilized onto each slide in a region apart from the biological sample. For example, the controls can be antigens, peptides, proteins or cells which are being tested for in the biological sample or can be a nucleic acid of known sequence if a hybridization assay is being preformed. These would act as positive controls which should give a signal or color if the assay works properly. Negative controls can also be placed onto the slide, e.g., a protein or antigen or a nucleic acid which should not react with the reagents in the well. For example, assume a person is to be tested for the presence of six antigenic determinants A-F. A six well tray can be used with each well containing a different antibody A'-F'. The six different antigenic determinants can be spotted onto all six slides. In all cases, only a single one of these controls should show as positive on each slide. Slide A should show only antigenic determinant A as a positive signal, slide B should show only antigenic determinant B as a positive signal, etc. These act as external controls. If more than one control shows as a positive, this indicates antibody cross reaction has occurred. If none of the controls is positive it indicates that the reaction did not work, e.g., a reagent may have been missing. The biological sample being tested acts as an internal control.

Figure 3:
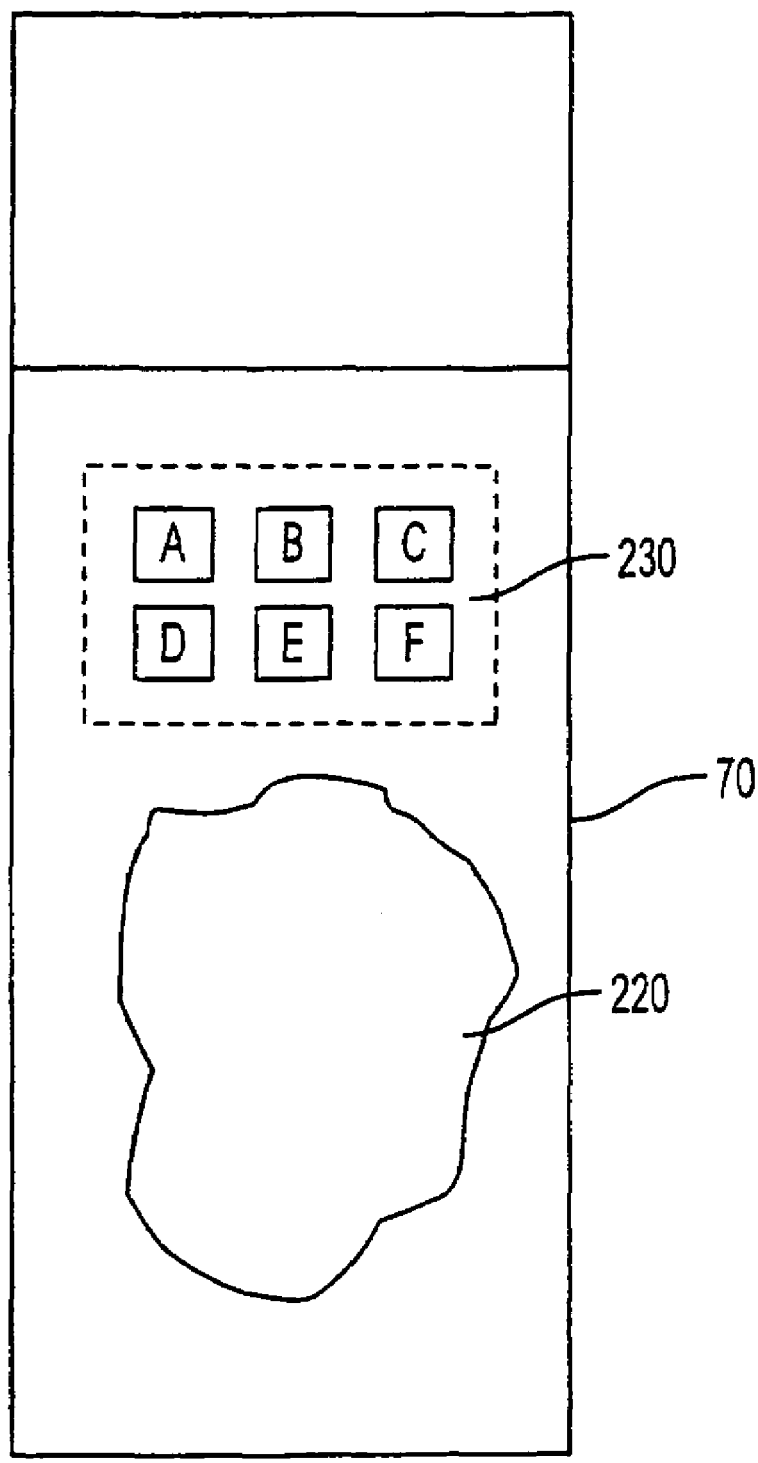
FIG. 3 illustrates a slide 70 with a biological sample 220 and a stamp 230. The stamp shown contains reagents A-F.

The external controls can be placed onto each slide by a variety of means. A preferred mode is to spot the reagents onto the equivalent of a postage stamp or sticker, which uses glue resistant to xylene and alcohol, which can then be glued onto each slide. Such a stamp or sticker can be made of any suitable material to which proteins, peptides, cells or nucleic acids bind tightly. This can include, but is not limited to, commonly used membranes such as nitrocellulose, plastic, glass or nylon. Specific examples of such membranous material are nitrocellulose itself, Immobilon-P (Millipore), Hybond-N, Hybond-N$^+$ and Hybond C-extra nitrocellulose (Amersham), Genescreen and Genescreen Plus (Du Pont), Clearblot-P (ATTO Co.) and polyvinyldifluoride membranes (Millipore or BioRad). The stamp or sticker will have regions A-F as shown in FIG. 3. These stamps or stickers can be premanufactured and stored until ready for use, the antigenic determinants, proteins, peptides, cells or nucleic acids being dried onto the stamps or stickers. The name of the antigen, protein, cell, etc., can be printed on the stamp or sticker. This is especially suitable for mass production. Standard sets of assays can be premade such as a panel to test for breast cancer or a panel to test for Hodgkin's disease, but one can always design any combination of reagents as external controls as are desired. A stamp of controls can be attached to a slide either prior to a biological sample being placed upon the slide or it may be delayed until the biological sample has been fixed on a slide and been processed to the point at which reactions relevant to the controls are to be performed.

The stamps can be color coded or numbered to indicate a specific panel of tests to be performed. In like fashion the tray 14 can be color coded or numbered or otherwise marked to indicate the panel of tests to be performed, this being dependent upon the predried reagents in the wells 24 of the tray 14. The stamp and the tray should match colors or numbers or other marking.

One other aspect of the invention is that reagents which are dried in wells 24 can be dried in layers in the reverse order which they are to act. When buffer is added the last added reagent will dissolve first and be active, followed by the next to last added reagent which acts in turn, etc. In this manner two or more reagents can be added to a single well 24 thereby allowing consecutive action of the reagents without the necessity of moving the slides 70 from one tray 14 to a second tray 14. For multistep reactions this will decrease the number of trays 14 which are necessary and also decreases the amount of labor involved.

Another aspect of the invention is a specially designed tray or chip which allows one to perform whole chromosome painting of all 24 human chromosomes on cells on a single slide.

Still another aspect of the invention is a tray and slide assembly wherein the volume of space in the well of the tray can be adjusted so that a small volume can be present to perform a reaction such as a PCR and then the volume of space can be increased to allow fluid to be pumped through the well.

Those of skill in the art recognize that the sample to be tested on the slide including the protein, peptide, DNA, RNA or cells or the control protein, peptide, DNA, RNA or cells on the stamp, must be immobilized so that they will not be released during the assay. The reagents which may have been predried in the tray, however, which reagents may include proteins, peptides, nucleic acids, etc., should be released, in a programmed order if multilayered once the water or buffer has been added.

EXAMPLES

In each example a biological sample is first mounted onto a microscope slide 70 and then assayed. Surgical and autopsy human biological samples from various organs (lymph node, liver, kidney, lung, breast, skin, prostate) were routinely fixed in 10% neutral buffered formalin, processed overnight on a tissue processor, and embedded in paraffin. Serial sections are cut at 4-5 microns and mounted onto Probe-On-Plus Slides (#15-188-52; Fisher Scientific) and dried overnight at room temperature. Slides 70 are then inserted into a reusable slideholder 1. At this point all the slides 70 in a single holder 1 (up to six slides) can be handled simultaneously. The slides 70 are deparaffinized by placing the slides 70 in a staining dish with four changes of xylene for 5 minutes each, two treatments of 100% ethanol for 1 minute each and two treatments of 95% ethanol for 1 minute each. The deparaffinized tissue section slides 70 are cleared and washed with deionized water.

The present invention is further detailed in the following Examples, which are offered by way of illustration and are not intended to limit the invention in any manner. Standard techniques well known in the art or the techniques specifically described below are utilized.

Example 1

Immunocytochemistry

In this Example a biological sample is treated with antibodies (primary and secondary), treated for chromogen color development, and finally counterstained.

A. Proteolytic Pretreatment of Mounted Tissue Samples

It is well known in the art that when using certain antibodies for immunocytochemical staining it is necessary to pretreat the formalin fixed tissue section with proteolytic enzymes such as 0.4% pepsin, pH 2.0. When this is necessary the following steps may be utilized. A few drops (150-200 μL) of the proteolytic digestion solution are placed on each well 24 of the 3 or 6 well tray 14. The tissue side of the slides 70 is faced down on the wells 24. The slideholder 1 with the slides 70 should be slowly laid down and placed on the wells 24 of the tray 14. No air bubbles should remain between the tissue side of the slides 70 and the solution in the wells 24 of the tray 14. The slides 70, slideholder 1 and tray 14 with solution are incubated for 15 minutes at 40° C.

If many samples are being processed at one time it is more efficient to forgo use of the tray 14 during this proteolytic pretreatment step. The slides 70 are still placed into slideholders 1 six to a holder 1. The slideholders 1 and slides 70 are then placed vertically into a staining dish with 500 mL of the proteolytic digestion solution (which may be reused) and incubated for 20 minutes at 40° C. in a water bath. Up to twenty slideholders 1 (120 slides) may be simultaneously placed into the staining dish for this pretreatment step.

Some antibodies require that the tissue section be pretreated with microwave antigen retrieval. Slideholders 1 (up to 20) with slides 70 are vertically placed into a staining dish with 500 mL of 0.01 M citrate buffer, the staining dish is placed in the center of a microwave oven, and the oven is turned to high power (800-850 Watts) for 7-8 minutes bringing the solution to a rapid boil. The oven is turned off, the power level is reset to 400 Watts, and the oven is turned on again to heat the solution for 7-8 minutes.

After proteolytic digestion and microwave treatment the tissue sections are washed in the staining dish with three 500 mL changes of phosphate buffered saline (PBS).

B. Treatment of Tissue Sections with Goat and Horse Serum

All slides 70, whether or not proteolytically digested and microwave treated, are incubated with 5% mixed normal goat and horse serum for 20-30 minutes at room temperature. Each well 24 of a tray 14 is filled (approximately 150-200 μL) with mixed normal goat and horse serum. The tissue side of the slides 70 is placed down on the wells 24 to contact the serum. The slideholder 1 should be slowly laid down so as to avoid trapping any air between the slides 70 and the wells 24. Again, if many samples are being processed at one time, it is more efficient to perform this step as a batch by placing up to 20 slideholders 1 vertically into a staining dish with 500 mL of 5% mixed normal goat and horse serum for 20-30 minutes.

C. Application of the Primary Antisera or Antibodies

Following incubation with the serum, the slideholder 1 and slides 70 as well as the tray 14 are put into a staining dish with PBS. The tray 14 is separated from the slideholder 1 and both are washed once with PBS. The washed tray 14 may be reused for the next step. Prediluted primary antisera or antibodies (approximately 150-200 μL) are applied to each well 24 of the tray 14. The washed slides 70, still in the slideholder 1, are placed tissue side down onto the wells 24. As always care must be taken to avoid trapping bubbles between the slide 70 and the reagent solution in the wells 24. The samples are incubated with the antisera or antibodies for 2-4 hours at room temperature or incubated in a humidity chamber at 40° C. for 2 hours or may be incubated in a humidity chamber at room temperature overnight. After incubation the slideholder 1 and attached slides 70 are removed from the tray 14 and are washed in a staining dish with PBS three times.

D. Application of the Secondary Antibody

Prediluted secondary antibody (approximately 150-200 μL) is applied into each well 24 of a new tray 14. The slides 70 in the slideholder 1 are placed onto the wells 24 tissue side down being careful to avoid bubbles. This is incubated for 30 minutes at 40° C. in a humidity chamber. After incubation the slideholders 1 and attached slides 70 are removed from the tray 14 and washed in a staining dish with three changes of PBS.

E. Treatment for Removal of Endogenous Peroxidase Activity

All slideholders 1 with attached slides 70 are placed into a staining dish with 500 mL of PBS with 3% hydrogen peroxide and 0.1% sodium azide, and incubated at room temperature for 15 minutes. After incubation with the hydrogen peroxide PBS the slideholders 1 and attached slides 70 are washed in a staining dish with three changes of PBS.

F. Application of the ABC Complex "ELITE"

The ABC complex (Vector Laboratories Inc., Burlingame, Calif.) is diluted to its working concentration using PBS. The working concentration (approximately 150-200 µL) is applied to each well 24 of a new tray 14. The slides 70 with attached slideholders 1 are carefully placed tissue side down onto the trays 14 so that no air bubbles are trapped between the solution and the slides 70. The slides 70 and trays 14 with ABC solution are incubated in the humidity chamber at 40° C. for 30 minutes. After incubation the slideholders 1 with attached slides 70 are removed from the trays 14 and washed in a staining dish with 3 changes of PBS.

G. Chromogen Color Development Using Diaminobenzidine (DAB)

DAB solution is prepared by adding 100 mg DAB to 100 mL PBS and adding 50 µL of 30% $H_2O_2$. Approximately 150-200 µL of the DAB solution is added to each well 24 of a new tray 14 to completely fill each well 24. The slides 70 with attached slideholders 1 are placed tissue side down onto the wells 24 being careful to avoid trapping air bubbles. Color development can be monitored by viewing the slideholders 1 and trays 14 with DAB under a microscope. A colored precipitate will form at the site of positive cells. Color begins to appear after 2-5 minutes, usually reaching sufficient development within 10 minutes, but a 20-30 minute incubation may be necessary for weakly stained samples. To stop development, all slideholders 1 with slides 70 are removed from the trays 14 and washed in a staining dish with three changes of deionized water.

H. Counterstaining

Slideholders 1 and attached slides 70 are immersed in Harris's hematoxylin for 10-50 seconds and washed by dipping into deionized water for three changes. Then all the slides 70 are immersed in 0.2% ammonium hydroxide solution for 30 seconds and washed by dipping in deionized water for 3 changes. The slides 70 are dipped into 95% ethanol for two changes of 2 minutes each, followed by dipping into 100% ethanol for 2 changes of 2 minutes each, and finally the slides 70 are cleared by dipping into two changes of xylene for 2 minutes each.

I. Attachment of the Coverslip

Place 1 drop of Cytoseal 60 or premount on the tissue section side of each slide 70 with the slides 70 still attached to the slideholder 1. Place coverslips onto each slide 70. Although this may be done one by one, it is more efficient to use a specially designed coverslip which is actually six (or three) conjoined coverslips properly spaced to align with six (or three) slides 70. Using this special coverslip, up to 6 individual coverslips are effectively aligned and placed onto slides 70 simultaneously. The coverslips are easily separated from the plastic strip holding them together simply by bending the coverslip which is prescored to allow the strip to snap apart from the coverslips which remain bound to the slides 70. At this point the slides 70 may be removed from the slideholder 1 to be handled individually, or they may be left attached to the slideholder 1 for ease of transportation.

FIGS. 10-12 of U.S. Pat. No. 5,958,341 (W.-S. Chu) show the results of a study comparing the use of the present invention with staining methods simply using the standard manual method of dropping reagents onto the surface of a slide-mounted tissue sample and leaving the reagents open to the atmosphere for incubation. The Figures show that the results obtained with the two methods are extremely comparable with the results obtained using the present invention being at least as good as, and apparently better than the results obtained using the traditional method. The present invention however allowed these results to be obtained with less work and with the use of smaller amounts of reagents.

Comparing the two methods, the background staining is significantly reduced by using the present invention, especially when using polyclonal antibodies (anti-kappa light chain antibodies and anti-lambda light chain antibodies). The invention significantly improves the staining results by reducing the background. Background is partially due to free FC fragments which precipitate by gravity and bind nonspecifically to the tissue. The present method inverts the slide such that the tissue is above the solution and therefore free FC fragments cannot precipitate by gravity onto the tissue.

Example 2

In Situ Hybridization

In this example biological samples are mounted onto slides 70, hybridized with biotin or digoxigenin labeled probes and reacted with anti-biotin or anti-digoxigenin antibody. The samples are then stained.

A. Preparation and Mounting of Tissue Sample

A tissue sample is prepared as described above but with extra measures to prevent nucleic acid degradation. A tissue sample is fixed in 10% neutral buffered formalin, processed overnight on a tissue processor, embedded in paraffin, cut into serial sections of 4-5 microns, mounted onto Probe-On-Plus Slides (#15-188-52; Fisher Scientific), and dried overnight at room temperature. The slides 70 are inserted into a slideholder 1 and are deparaffinized by placing into a staining dish. The slides 70 are treated with four changes of xylene for 5 minutes each, two changes of 100% ethanol for 1 minute each and two changes of 95% ethanol for 1 minute each. The deparaffinized tissue section slides are then cleared and washed with deionized water with RNase Block (BioGenex, San Ramon, Calif.).

B. Proteinase K Treatment of the Mounted Tissue Samples

Approximately 150-200 µL of freshly diluted proteinase K solution is placed into each well 24 of a tray 14 to completely fill each well 24. The microscope slides 70 (still in the slideholder 1) are placed onto the wells 24 with the tissue side down. The slides 70 are placed onto the wells 24 carefully so as to avoid the presence of air bubbles between the solution in the wells 24 and the slide 70. This is incubated for 15 minutes at room temperature.

After digestion, the slideholders 1 with slides 70 attached are removed from the tray 14 and washed in a staining dish with 500 mL of PBS with RNase Block for 5 minutes. The tissue section slides 70 are dehydrated by immersing in a staining dish serially in the following solutions: 500 mL distilled water plus RNase Block for 10 seconds, 500 mL 50% ethanol plus RNase Block for 10 seconds, 500 mL of 95% ethanol for 10 seconds, and 500 mL 100% ethanol for 10 seconds. The slides 70 are dried at room temperature for 5 minutes.

C. Hybridization with Biotinylated or Digoxigenin Labeled Probes

Trays 14 with shallow wells 24 (0.02-0.08 mm in depth) may be used here to conserve materials. Hybridization solution containing a biotinylated or digoxigenin labeled oligonucleotide probe is placed into each well 24 of a tray 14. Enough solution is added to each well 24 to completely fill the well 24. This requires approximately 50-100 µL of solution. The slides 70 are placed on top of the wells 24 (3 or 6 at a time still attached to the slideholders 1) being careful not to trap any air bubbles. The trays 14 plus slideholders 1 and slides 70 are placed in an oven or on a heating block at 95° C. for 8-10 minutes to denature the nucleic acids. This step eliminates hair-pin loops or folding back of mRNA sequences. After the denaturation step, the slides 70 are incubated in a humidity chamber at 45° C. overnight. Following the hybridization step, the slides 70 are washed by removing the slideholders 1 with attached slides 70 from the trays 14 and washing the slides 70 in a staining dish with 2×SSC (standard saline citrate) at 37° C. for 5 minutes followed by a wash with 1×SSC at 37° C. for 5 minutes. This is followed by a 30 minute wash in 0.2×SSC at 60° C. Finally the slides 70 are washed with 2 changes of PBS for 2-5 minutes each.

D. Signal Detection

The slideholders 1 with attached slides 70 are placed vertically into a staining dish with 500 mL of 5% mixed normal goat and horse serum at room temperature for 20 minutes. Prediluted mouse anti-biotin or mouse anti-digoxigenin antibody (150-200 μL) is applied to each well 24 of a new tray 14. The slides 70 are placed onto the wells 24 of the tray 14 taking care to avoid trapping bubbles. The slides 70 and trays 14 with antibody are incubated in a humidity chamber at 40° C. for 2 hours.

After incubation with the anti-biotin or anti-digoxigenin antibody, the slideholders 1 with slides 70 are removed from the trays 14 and washed in a staining dish with three changes of PBS.

E. Application of the Secondary Antibody

Prediluted secondary antibody (approximately 150-200 μL) is applied into each well 24 of a new tray 14. The slides 70 in the slideholder 1 are placed onto the wells 24 tissue side down being careful to avoid bubbles. This is incubated for 30 minutes at 40° C. in a humidity chamber. After incubation the slideholders 1 and attached slides 70 are removed from the tray 14 and washed in a staining dish with three changes of PBS.

F. Treatment for Removal of Endogenous Peroxidase Activity

All slideholders 1 with attached slides 70 are placed into a staining dish with 500 mL of PBS with 3% hydrogen peroxide and 0.1% sodium azide, and incubated at room temperature for 15 minutes. After incubation with the hydrogen peroxide PBS the slideholders 1 and attached slides 70 are washed in a staining dish with three changes of PBS.

G. Application of the ABC Complex "ELITE"

The ABC complex is diluted to its working concentration using PBS. The working concentration (approximately 150-200 μL) is applied to each well 24 of a new tray 14. The slides 70 with attached slideholders 1 are carefully placed tissue side down onto the trays 14 so that no air bubbles are trapped between the solution and the slides 70. The slides 70 and trays 14 with ABC solution are incubated in the humidity chamber at 40° C. for 30 minutes. After incubation the slideholders 1 with attached slides 70 are removed from the trays 14 and washed in a staining dish with 3 changes of PBS.

H. Chromogen Color Development Using Diaminobenzidine (DAB)

DAB solution is prepared by adding 100 mg DAB to 100 mL PBS and adding 50 μL of 30% $H_2O_2$. Approximately 150-200 μL of the DAB solution is added to each well 24 of a new tray 14 to completely fill each well 24. The slides 70 with attached slideholders 1 are placed tissue side down onto the wells 24 being careful to avoid trapping air bubbles. Color development can be monitored by viewing the slideholders 1 and trays 14 with DAB under a microscope. A colored precipitate will form at the site of positive cells. Color begins to appear after 2-5 minutes, usually reaching sufficient development within 10 minutes, but a 20-30 minute incubation may be necessary for weakly stained samples. To stop development, all slideholders 1 with slides 70 are removed from the trays 14 and washed in a staining dish with three changes of deionized water.

I. Counterstaining

Slideholders 1 and attached slides 70 are immersed in Harris's hematoxylin for 10-50 seconds and washed by dipping into deionized water for three changes. All the slides 70 are immersed in 0.2% ammonium hydroxide solution for 30 seconds and washed by dipping in deionized water for 3 changes. The slides 70 are then dipped into 95% ethanol for two changes of 2 minutes each, followed by dipping into 100% ethanol for 2 changes of 2 minutes each, and finally the slides 70 are cleared by dipping into two changes of xylene for 2 minutes each.

J. Coverslipping

Place 1 drop of Cytoseal 60 or premount on the tissue section side of each slide 70 with the slides 70 still attached to the slideholder 1. Place coverslips onto each slide 70. Although this may be done one by one, it is more efficient to use a specially designed coverslip which is actually six (or three) conjoined coverslips properly spaced to all line up with six (or three) slides 70. Using this special coverslip, up to 6 individual coverslips are effectively aligned and placed onto slides 70 simultaneously. The coverslips are easily separated from the plastic strip holding them together simply by bending the strip which is prescored to allow the strip to snap apart from the coverslips which remain bound to the slides 70. At this point the slides 70 may be removed from the slideholder 1 to be handled individually, or they may be left attached to the slideholder 1 for ease of transportation.

Example 3

PCR In Situ Hybridization

Polymerase chain reaction (PCR) was developed as an in vitro method for amplifying small amounts of specific pieces of nucleic acids. This was later adapted to in situ studies so that there was amplification of nucleic acid within tissue sections. The apparatus of the present invention is suited to performing these in situ PCRs. An example of a PCR in situ hybridization protocol is given in Nuovo (1994).

A. In Situ PCR

Serial tissue sections are cut at 4-5 microns thickness, mounted onto Probe-On-Plus slides 70, and dried overnight at room temperature. The mounted tissue sections are deparaffinized and digested with pepsin at 40° C. for 15-90 minutes depending on the length of time of fixation in formalin. The pepsin is inactivated by washing the slides 70 in diethylpyrocarbonate (DEPC) treated water for one minute followed by a one minute wash in 100% ethanol. The slides 70 are then air dried.

Polymerase chain reaction solutions are made according to any standard procedure. See, e.g., K. B. Mullis et al., U.S. Pat. No. 4,800,159. Combine buffer, 5' and 3' primers, water, Taq polymerase (AmpliTaq, Perkin Elmer) (or other thermophilic polymerase) and Self-Seal Reagent (MJ Research, Inc.) in a total volume of 20-50 μL. Apply the 20-50 μL of solution to a well 24 of a specially designed in situ PCR aluminum tray 14. The trays 14 to be used in Example 1 are preferably made of a disposable plastic material, but the trays 14 used for PCR studies must be capable of being cycled through a series of temperatures which may reach 95-100° C. Therefore it is necessary for such trays 14 to be heat resistant (i.e., they should not melt or otherwise be destroyed by high temperatures) and also to be good conductors of heat. Aluminum is a preferred material from which to manufacture these trays 14. These aluminum trays 14 have wells 24 which are 0.005-0.03 mm in depth and hold approximately 20-50 µL of solution.

After completely filling each well 24 of the aluminum tray 14, the slideholder 1 and attached slides 70 are placed on top of the tray 14 with the tissue section facing down so as to contact the solution in the well 24 upon which it is placed. Care must be taken to avoid air bubbles being present between the solution and the slide. The slideholder 1, slides 70 and aluminum tray 14 are then placed onto a block of a thermal cycler at 95° C. for 3-5 minutes to denature the nucleic acids in the tissue. Twenty to thirty cycles are then performed cycling between 60° C. for 2 minutes and 94° C. for 1 minute.

Following the cycling steps, the slideholder 1, slides 70 and aluminum tray 14 are placed vertically into a staining dish with 2×SSC at 37° C. for 5 minutes. The slideholder 1 is removed from the aluminum tray 14 and washed with 0.5-1× SSC at 37-60° C. for 10-30 minutes (depending upon background). In situ hybridization is performed as described in Example 2 using a biotinylated or digoxigenin labeled probe chosen internal to the primers.

B. Reverse Transcriptase In Situ PCR

Serial tissue sections are cut at 4-5 microns thickness, mounted onto Probe-On-Plus slides 70, and dried overnight at room temperature. An important aspect of the RT in situ PCR is that both negative and positive controls be performed and it is preferred that these be performed on the same glass slide. The positive control omits the DNAse digestion step and should generate an intense nuclear signal from target specific amplification, DNA repair and mispriming. The negative control uses a DNAse treatment plus primers that do not correspond to a target in the cells. The test sample undergoes DNAse treatment but uses primers specific to the desired target nucleic acid. The mounted tissue sections are deparaffinized and digested with pepsin at 40° C. for 15-90 minutes depending on the length of time of fixation in formalin. The pepsin is inactivated by washing the slides 70 in diethylpyrocarbonate (DEPC) treated water for one minute followed by a one minute wash in 100% ethanol. The slides 70 are then air dried.

Digest two of the three mounted tissue sections with RNase-free DNAse by filling each well 24 of a plastic tray 14 (requiring approximately 150-200 µL) with prediluted RNase-free DNAse and placing the slides 70 (in the slideholder 1) tissue side down on top of the well 24 being careful that air bubbles are not trapped and that contact is made between the solution in the well 24 and the tissue sample. Incubate overnight at 37° C. Inactivate the RNase-free DNAse with a 1 minute wash in DEPC water and a 1 minute wash in 100% ethanol. Let the slides 70 air dry.

The reverse transcription is performed using the EZ RT PCR system (Perkin Elmer). The RT/amplifying (RT-PCR) solution contains EZ rTth buffer, 200 µM each of dATP, dCTP, dGTP and dTTP, 400 µg/mL bovine serum albumin, 40 Units RNasin, 0.8 µM of 5' and 3' primers, 2.5 mM manganese chloride, 5 Units of rTth, and 2× concentrated Self-Seal Reagent (MJ Research, Inc.). Twenty to fifty µL of the RT-PCR mixture is placed into each of three wells 24 in a specially designed in situ PCR aluminum tray 14 (the depth of the wells 24 is approximately 0.005-0.03 mm) to fill the wells 24. The slides 70 are carefully placed onto the wells 24 with the tissue being placed in contact with the solution inside of the well 24. The slides 70, slideholder 1 and aluminum tray 14 are placed onto a block of a thermal cycler at 65° C. for 30 minutes followed by a denaturation step at 94° C. for 3 minutes. Twenty to 30 cycles are performed, each cycle being 60° C. for 2 minutes followed by 94° C. for 1 minute.

Following the cycling steps, the slideholder 1, slides 70 and aluminum tray 14 are placed vertically into a staining dish with 2×SSC at 37° C. for 5 minutes. The slideholder 1 is separated from the aluminum tray 14 and washed with 0.5-1×SSC at 37-60° C. for 10-30 minutes (depending upon background). In situ hybridization is performed as described in Example 2 using a biotinylated or digoxigenin labeled probe chosen internal to the primers.

Those of skill in the art recognize that amplification schemes other than PCR are now well known and widely used and can be used in place of PCR. These include ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). See, e.g., U.S. Pat. Nos. 4,683,195 and 4,683,202 and Innis et al. (1990) for PCR; Wu and Wallace (1989) for LCR; U.S. Pat. Nos. 5,270,184 and 5,455,166 and Walker et al. (1992) for SDA; Spargo et al. (1996) for thermophilic SDA and U.S. Pat. No. 5,409,818, Fahy et al. (1991) and Compton (1991) for 3SR and NASBA.

Example 4

Wells with Multilayered Dried Reagents

Assays can be performed with a single reagent predried in a well 24 and if the use of several reagents is required, the slide 70 with biological sample can be moved from a first well 24 with the first reagent to a second well 24 with the second reagent, etc., wherein the various wells 24 can either be on the same or on separate trays 14. Alternatively, more than one reagent may be predried in a well 24. The reagents can be dried in layers with the outermost layer being the first reagent to be used. This is demonstrated in FIG. 4 which shows a slide 70 with cells or tissue section 220 placed over a well 24 into which has been predried in order: a secondary antibody 270, a primary antibody 260, and a protein blocking reagent 250. In this manner, different reagents are separated and dry stored thereby preventing reaction until the addition of water or buffer to the well. Upon addition of water (if salts are predried in the well) or buffer to the well, the protein blocking agent 250 will dissolve first since it was in the final layer of reagents predried in the well 24. Next the primary antibody 260 will dissolve and finally the secondary antibody 270 will dissolve and be able to react. Such a system allows all three steps to occur without the necessity of moving the slides 70 from one tray 14 to another tray 14 or from one well 24 to another well 24. For a different type of assay, for example one which requires a series of four reagents, one may either predry all four reagents in reverse order of action in a single well 24 or it may be found that the use of two trays each with two reagents or one tray with three reagents and a second tray with either the first or fourth reagent works better, for example when a wash step is needed between the step or steps of the first tray and the step or steps of the second tray. Other variations on these schemes are obvious to one of skill in the art. Any such combination requires less manual labor then the use of four separate trays. Especially in the field of pathology for which the types of assays to be performed are well standardized, such a system is quite amenable to mass production of trays with predried reagents which can then be stored until time of use. This system is not limited to the use of antigen/ antibody reactions but can also be used for other reactions, e.g., enzymes can be dried in the wells, nucleic acid hybridization can be performed with different probes dried in the wells, a fluorescent probe can be the dried reagent, biotin can be dried in the well, etc.

To prepare wells with multiple layers of different reagents, it is preferred to include layers of inert material between the layers of reagents. For example, a well may be coated with reagents as follows. A secondary antibody is coated onto a well and allowed to dry. On top of this is coated a high concentration of an inert material (i.e., a material not necessary for any of the reactions and which will not interfere with the reactions) such as bovine serum albumin, gelatin, sucrose, fetal calf serum, starch, agarose or other inert material. This is allowed to dry. It is preferred that the inert material be added in several layers, e.g., gelatin in solution is added, allowed to dry, then more gelatin in solution is added, allowed to dry, etc. This can be performed as often as desired, the number of layers affecting the delay time until the release of the secondary antibody. Five such coatings on top of the secondary antibody has been found to give good results with a delay of about 15-20 minutes until the release of the secondary antibody from the time this inert layer begins to dissolve. On top of this first layer (or multilayer) of inert material is coated a primary antibody which is allowed to dry. On top of the primary antibody is coated a second layer or multilayer of inert material. This can be a low concentration of bovine serum albumin, gelatin, fetal calf serum, starch, agarose or other inert material. Three coatings of this second inert layer has been found to yield good results with a delay time of about 10 minutes until the release of the primary from the time the second inert layer begins to dissolve. On top of the second inert layer is coated a protein block such as horse and goat serum. The protein block is allowed to air dry. The multilayers of inert material take time to dissolve thereby giving each reaction enough time to occur prior to the next layer of active reagent dissolving.

The limitation of this system is that it can only be used for a series of steps which do not require a wash step in between successive steps. For example, if reaction with a primary antibody is followed by reaction with a secondary antibody, the secondary antibody must be washed off prior to the detection step. Therefore the detection reagent cannot be predried in the same well as the secondary antibody. Similarly, if one step requires heating (e.g., denaturation of a nucleic acid probe) this cannot be combined with a reagent which is heat inactivated or destroyed.

Example 5

Built-In Controls and Automated Labels

Immunoassays or ISH/Fish

When assays are performed in a clinical setting, controls are required by the Food and Drug Administration. Having built-in controls on the very slides being assayed is an excellent manner in which to test the controls. If the control is on a completely different slide, the control is not as good because it cannot indicate whether there was a problem such as reagent not contacting the biological sample on either the control or the actual test sample or missing a step of adding a reagent to either the control or the test sample. Also, the reagents dropped onto the control sample may accidentally be different from those dropped onto the test sample by a human or by machine error, especially when several tests are being performed simultaneously. When the control is on the same slide as the test sample, such problems will be indicated by controls, but if the control is a section of normal or neoplastic tissue it is very labor intensive and time consuming to prepare the control sample.

FIG. 3 illustrates a slide 70 onto which a tissue slice 220 has been fixed and also illustrates a separate region of slide 70 onto which has been affixed a stamp or sticker 230 (e.g., a piece of nitrocellulose or other membrane or plastic or glass type matrix glued onto the slide 70) with six distinct regions A-F, although the use of a stamp or sticker is not essential, e.g., the controls can be directly coated onto the slide 70. Each region of A-F has been spotted with, e.g., a distinct antigenic substance or nucleic acid, depending on the type of assay being performed, although these substances can be applied directly to a region of the slide 70 in lieu of using a stamp or sticker 230. Six separate assays are to be performed using a six well tray. Each well 24 will have a reagent A'-F' which reacts, respectively, with A-F. Control A should be positive only on the slide 70 placed onto well 24 with reagent A' and should be negative for the remaining 5 wells. Control B should be positive only on slide 70 placed onto the well 24 with reagent B' and should be negative for the other 5 wells, etc. The stamps or stickers 230 with these external controls can be premade commercially for mass sale or they can be custom made. It is also useful if a stamp or sticker 230 for a common clinical panel of assays is color coded or otherwise labeled so that a quick glance is indicative of the assays being performed. This color code or other labeling can also be matched to the color code or other labeling of trays 14 to be used in conjunction with the stamp, e.g., a green stamp will have antigenic determinants A-F on it and a green tray will have antibodies A'-F'. A numbering or lettering system can be used as one alternative to a color coding scheme. These could be used for a series of tests for breast cancer whereas a red stamp and red tray could indicate those to be used to assay for Hodgkin's disease. Any type of color coding, such as a series of stripes of colors, can be used. Such color coding will result in fewer errors being made in the clinical laboratory. The use of the positive control on each slide also acts as an automatic labeling system for the slide since the positive external control is indicative of the assay performed for that slide. If desired, the stamps can be packaged with their corresponding trays and can even be placed onto each tray when packaged and then peeled from the tray and placed onto a slide at the time of use. The use of such stamps or stickers with controls on them is much simpler and less time consuming than preparing a control biological sample, e.g., a tissue section of normal or neoplastic tissue, to be used as such a control.

As an example, a breast panel of assays can be performed in which six distinct diagnostic markers are used. These diagnostic markers can be cytokeratin 7, cytokeratin 20, ER, Bcl-2, PR, and cathepsin D. Each of these antigenic determinants can be coated onto a stamp or sticker to be used as controls and the corresponding antibodies can be predried on separate wells of a 6 well tray. If cytokeratin 7 or an equivalent antigenic determinant is placed on position A of the stamp or sticker, then antibody against cytokeratin 7 is to be placed in well A'. Section A of the stamp or sticker should be positive on the slide placed on well A' but should be negative on the other 5 wells. Also, only section A of the stamp should be positive on the slide 70 placed on well A', while sections B-F of the stamp or sticker should be negative. This results in the automatic labeling of the slide by the built-in control. If section A is not positive or if any of sections B-F are positive on this slide it means that a problem has occurred and the test should not be relied upon.

Other examples of panels which may be used are a panel of prognostic markers for breast cancer such as Ki-67, Her-2/neu (c-erbB-2), P53, pS$_2$, EGFR, and Factor VIII. Other neoplasms, e.g., prostate, bladder and colon can also use the same prognostic panel tray. In general pathology practice, four panel trays can cover 90-95% of diagnoses of all hemopoietic diseases: 1) A Hodgkin's disease panel may include the markers LCA (CD45). L26 (CD20). CD3, Leu-M 1 (CD15), Ki-1 (CD30), and LMP. 2) A non-Hodgkin's panel can include L26 (CD20), CD3, MT1, Bcl-1, Bcl-2, Ki-1 (CD30). 3) A separate non-Hodgkin's panel can include Kappa, Lambda, UCHL-1 (CD45RO), CD5, CD23, and CD10. 4) A leukemia panel can include L26 (CD20), CD34, MPO, Lyso, TdT, and DBA44. Any other desired panel of tests can be similarly performed, such as but not limited to, panels for undifferentiated tumor of unknown primary site, sarcoma classification, lymphoma vs. carcinoma vs. melanoma, adenocarcinoma vs. mesothelioma, hepatocellular/cholangiocarcinoma vs. metastatic carcinomas pituitary panel, Paget's disease vs. melanoma vs. squamous cell carcinoma vs. fibrous histiocytoma breast panel, and bladder vs. prostate carcinoma. Yet other possible panels are a neuroendocrine panel, small round cell tumor, germ cell tumor, Hodgkin's vs. non-Hodgkin's lymphoma, lymphoma vs. reactive hyperplasia, plasma cell dyscrasia, leukemia panel and a virus panel.

Each laboratory can devise its own system which is most appropriate to the personnel and to the number and types of assays being performed. For example, if an assay requires use of a first set of antibodies followed by reaction with a secondary antibody wherein the secondary antibody is identical for all samples, then if a small number of assays are to be performed one may do these on the trays 14, but if a large number of assays are being performed one may prefer to place all the slides into a large tank with the secondary antibody and/or detection system (a "batch" or "bulk" incubation method. Alternatively, for the lab doing a small number of assays, it is possible to coat a piece of filter paper with the secondary antibody and/or detection system, lay all the slides onto the filter papers and wet the filter paper at the time of use. This can be less expensive than using the trays. Similarly, nucleic acid probes can be placed onto the filter paper.

Example 6

Built-In Controls

Nucleic Acid Hybridization

In a manner similar to that discussed in Example 5 for immunoassays, built-in controls can be used for nucleic acid assays such as ISH or fluorescent in situ hybridization (FISH). In one type of FISH, fluorescent probes are used which illuminate large portions of the chromosomes. This is referred to as whole chromosome painting (WCP). This technique is useful for observing gross chromosomal aberrations such as translocations. The probes used can be in conjunction with a variety of different colored fluorophores. For example, probes to chromosome 1 can fluoresce orange, probes to chromosome 2 can be made to fluoresce green and probes to chromosome 3 can use a red fluorescing fluorophore. It is therefore possible to stain for all three chromosomes simultaneously and still be able to easily distinguish them from each other. In human cells, there can be up to 24 distinct nuclear chromosomes, these being chromosomes 1-22, X and Y. If three different fluorophores are used, all 24 chromosomes can be studied by using only 8 different tissue sections or 8 different sets of cells. These can be studied on 8 separate slides or if desired several tissue sections or sets of cells can be placed on separate sections of a single slide. It is possible to place 8 tissue sections on a single slide and thereby study all 24 chromosomes on a single slide with all reactions being performed simultaneously using 8 different sets of three mixed probes. These can be tested on a single cell smear slide by placing the slide on a tray or chip with 8 separate wells wherein each well has had predried in it a different set of 3 probes. Using microarray techniques, 24 built-in controls will be directly coated on the slide such that they will surround, within the inner borders, each well region (see FIG. 6E). One of skill in the art recognizes that it is not necessary to use 8 sets of 3 probes. Other variations are possible such as 6 sets of 4 differently labeled probes. It is also not necessary to use trays with predried reagents, rather the reagents can be added to the trays in liquid form. In a similar fashion, other techniques, such as in situ hybridization, can be performed using a desired number of controls which have been directly coated onto the slide in the region surrounding the inner borders of the wells. Although the controls have been shown as placed on the slide so as to surround the edges of the wells, such a pattern is not required and other patterns of arranging the controls can be used so long as they are in a region which contacts the reagents in the wells.

Example 7

Automated Multiwell Tray and Machine

Analysis of biological samples is very labor intensive, even with the use of automated systems since the automated systems still require several steps to be performed manually. A multiwell tray, or a multiwell tray with predried reagents, attached to tubing and a pump or pumps or connected to an automated processing machine can be used to partially or completely automate the processing of biological samples. Such a multiwell tray can be similar in design to the tray 14 discussed earlier. But the automated multiwell tray 330 (see FIGS. 5A-B) is used for steps such as washing or with less expensive reagents which can be used in larger amounts. The reaction chamber 280 of the automated multiwell tray 330 is designed to hold volumes such as 0.01-1 mL, although this amount is not critical and can be larger or smaller. The well includes one or more inlets and one or more outlets to accommodate tubing. The tubing entering an inlet is attached to a pump. A slideholder 1 with attached slides 70 is placed on top of the automated multiwell tray 330 and fluids can be pumped into the reaction chambers 280 through an inlet such as 300 or 302. Reagents can be recirculated during the reaction time and reused if desired (e.g., as shown in FIG. 5B) by using a pump 290 and tubing 295 through inlet 302 in conjunction with tubing 310 through outlet 294. Alternatively one can send the used material directly to a waste container 291 or a sink or to be analyzed, such as on a gel or by other instrumentation, via outlet 296. Circulated reagents can reduce incubation or reaction time and reduce background. The concentration of circulated reagents also can be gradually increased or decreased to reach the optimal reactive condition, especially when using multiple probes. This is especially applicable when a soft bottom tray is used which allows the use of varied volumes.

A central processing unit 286 controls the pumping of reagents and can open and close valves on various pieces of tubing attached to a pump so that one pump can control several different reagents or alternatively multiple pumps can be used all controlled by the central processing unit. With this setup, a slideholder with slides and mounted biological samples can be placed onto a multiwell tray, the central processing unit can be activated to pump desired fluids and reagents into the reaction chambers either recirculating the fluids or disposing of the fluids directly. Different reagents can be pumped into the reaction chamber sequentially without the need of a person transferring the slides from one tray to another tray. For example, slides with biological samples can be placed onto the automated multiwell tray and the system can pump in the reagents: xylene, 100% ethanol, 90% ethanol, hydrogen peroxide, a secondary antibody, detection reagents (ABC), diaminobenzidine, hematoxylin, PBS wash solution between each step, and the further 90% ethanol, 100% ethanol and xylene and a coverslipping solution. The slides can be removed from the automated multiwell tray for any desired intervening steps for which it is desirable to have the reaction performed on a regular multiwell tray 14 as described earlier.

As another example, slides with a mounted tissue section can be deparaffinized and treated separately and then placed onto a multiwell tray which has predried reagents and then be attached to the automatic processing machine which will pump in the desired reagents, e.g., secondary antibody, detection reagents (ABC), diaminobenzidine and hematoxylin as well as PBS wash buffer between each of these steps, followed by 90% ethanol, 100% ethanol, xylene and a coverslip solution.

The use of the automated multiwell tray has several advantages. It allows several steps to be done in succession with no manual labor required at each step. It also is safer because some dangerous chemicals, e.g., xylene and diaminobenzidine which are carcinogens, can be pumped directly from a container into the reaction chamber and from there into a waste receptacle or a receptacle from which the reagents can be reused without the need of a person pipetting these reagents into wells and handling the trays with these carcinogens on them. Recycling of such reagents using the prior art method of simply dropping reagents on top of biological samples mounted on slides is impracticable. Therefore the automated multiwell tray reduces exposure to hazardous chemicals, makes it easy to dispose of hazardous chemicals, and also reduces use of such chemicals because they can be reused and recycled.

The central processing unit 286 can also control heating and cooling of a heat block 288 to perform automated in situ PCR or to denature a probe being used for in situ hybridization. PCR reagents, including biotin or digoxigenin if desired, and primer sets can be coated and dried onto the wells of the tray 330. The slide 70 with sample 220 is placed onto the tray 330 and water or buffer is added. The heating block 288 can be placed against the slide 70 (as shown in FIG. 5B) or the tray 330 or can be one designed to contact both sides of the slide plus tray assembly and can be controlled by the central processing unit 286. Two results can be obtained from each well 410. First, fluid from a well 410 can be removed and assayed on a gel 298 to determine whether a band of DNA is seen. The size of any such band can also be determined on the gel 298. This acts as a control to see whether the PCR has worked successfully. This is possible because a large fraction of the amplified DNA does not remain in the cells of the sample but leaks out to the fluid in the well. Second, a fraction of the amplified DNA remains in the cells and this can be observed by detecting the biotin or digoxigenin by methods well known to those of skill in the art. Thus an in situ PCR shows which cells are detected by the assay.

The present invention also uses a novel modification which allows one to recover the reaction fluid and to assay this fluid, prior to continuing the work-up of the tissue sample, to determine whether the PCR has worked properly or has been contaminated. This assay is extremely quick and simple, e.g., simply running the reaction fluid on an agarose gel and looking for the presence of a specific band size. In the event that one determines that the PCR did work properly, then it is worth continuing the workup of the tissue sample. However, if it is determined that the PCR failed, one knows that it is not worth the labor and expense of continuing with the particular sample.

The above noted ability to assay the reaction fluid is useful not only for determining whether it is worth continuing to workup the specific sample, but this ability also yields data not available from viewing only the in situ hybridization results within the tissue. When in situ hybridization is performed, some fraction of amplicons remains where it was amplified while the rest ends up in the solution. By assaying the portion in solution, one can determine not only a relative amount of nucleic acid, but one is also able to determine the size of the amplified nucleic acids. When one views only the tissue sample one cannot determine the size product which is formed, one learns only that some nucleic acid was amplified and one also learns which cells were expressing the nucleic acid. These two sets of data are complementary. It is apparent that the present invention allows one to view both sets of results with the data of both being complementary. To date no apparatus has been available which had allowed one to obtain both types of data from a single polymerase chain reaction.

A further aspect of the invention is that the volume of the reaction chamber 280 is adjustable. Preferably a central processing unit 286 controls a piston 284 which pushes against reaction chamber bottom 282 which is either flexible or movable. This movement adjusts the volume of space in the reaction chamber 280. For example, when performing in situ PCR, it is desirable to keep the reaction volume very small, e.g., 10-50 µL. Following the PCR reaction it may be desired to pump the reaction fluid out of the reaction chamber. However, such a small volume of fluid will be held between the slide 70 and reaction chamber bottom 282 by capillary action. By allowing the reaction chamber to be enlarged to encompass more fluid, it becomes easier to accomplish the desired pumping. Those of skill in the art recognize that a variety of means can be used to adjust the volume of the reaction chamber 280. It is not necessary to use a piston controlled by a central processing unit. For example a screw means can be placed against the reaction chamber bottom and by turning the screw means the screw means will press against the tray bottom to force the bottom of the reaction chamber toward the microscope slide to reduce the volume of the reaction chamber 280. Reversal of this process again enlarges the volume.

Example 8

Whole Chromosome Painting

Chromosomes can be examined for gross abnormalities such as translocations by a technique known as whole chromosome painting. This method uses a number of fluorescently labeled probes which bind to a chromosome effectively to "light up" the whole chromosome. Sets of probes specific for each chromosome can be used to study any desired chromosome. Humans have a total of 24 nuclear chromosomes, these being chromosomes 1-22, X and Y. It is common to paint multiple chromosomes at one time. The chromosomes are easily distinguished by using fluorescent probes of different colors. For example, chromosomes 1, 2 and 3 can be stained simultaneously by using probes which fluoresce orange for one chromosome, probes which fluoresce green for a second chromosome, and probes which fluoresce red for a third chromosome. Using such a system, one test would typically use 8 slides of cells to examine the complete nuclear genome of a human. This test would include the placing the 8 slides onto 8 wells of a tray. One example of tissue to be assayed is a blood or bone marrow smear. The probes can be predried in the wells if desired.

A chip or tray 400 designed to allow the analysis of all 24 chromosomes on a single slide 70 is presented here. The tray 400 is one which can snap on to or otherwise be attached to a microscope slide 70. The chip or tray 400 contains 8 wells 410 with each well 410 separated from neighboring wells 410 by a gap or a trough 420. Such a tray 400 is illustrated in FIG. 6A. Each well 410 in the tray 400 has a narrow opening 430 through which reagents can be added to the wells 410.

In practice, cells to be examined are dropped or spread across a microscope slide 70. The slide 70 is then attached to the tray 400 such that the cells are facing the wells 410 of the tray 400. Reagents are then added to each well 410 individually through the opening 430 in the tray to each well 410. The reagents will spread between the well 410 and the slide 70 by capillary action. Different reagents specific for the various chromosomes are added to each well 410. The gap or trough 420 between wells 410 prevents the reagents from one well 410 spreading to a neighboring well 410 thereby preventing cross-contamination. The wells 410 hold a predetermined amount of fluid, e.g., 10-20 µL each, and capillary action allows only enough buffer to be added to fill the wells 410 without causing excess overflow. This aids in preventing cross-contamination. Three different chromosomes can be assayed in each well 410 using, e.g., orange, green and red fluorescent probes thereby allowing all 24 human nuclear chromosomes to be assayed on a single slide 70.

In a preferred embodiment, the probes are predried onto the 8 wells 410 of the tray 400 with probes for 3 different chromosomes in each well 410. If desired, other reagents such as salts can also be predried into each well 410. Metaphase or interphase cells are fixed across a slide 70 and the slide 70 is placed in contact with the tray 400. Then buffer is added to the openings 430 to each well 410. With this method, there is no necessity to pipet the different reagents into each well 410, rather the same buffer is added to all wells 410 thereby preventing the possibility of pipetting incorrect reagents (human error) into wells 410. The predried probes and salts dissolve upon addition of buffer to the wells 410 and hybridization is allowed to occur. A typical incubation may be at 70-90° C. for 1-2 minutes to denature the probes as well as the cellular DNA followed by an incubation at 37-45° C. for approximately 2 hours, although it is common to perform incubations for anywhere from 30 minutes to overnight. The hybridization buffer can be chosen as desired with several buffer systems commonly used in the art. For example 2× SSC is commonly used. Formamide is sometimes added to the buffer. In a preferred embodiment, following incubation the tray 400 can be placed onto a blotting material, e.g., paper towels, and the reaction fluid in the wells 410 will be physically removed from the wells 410 by capillary action, the blotting material soaking up the hybridization fluid. This prevents cross-contamination between wells 410 when the slide 70 is separated from the tray 400.

Figure 6E:
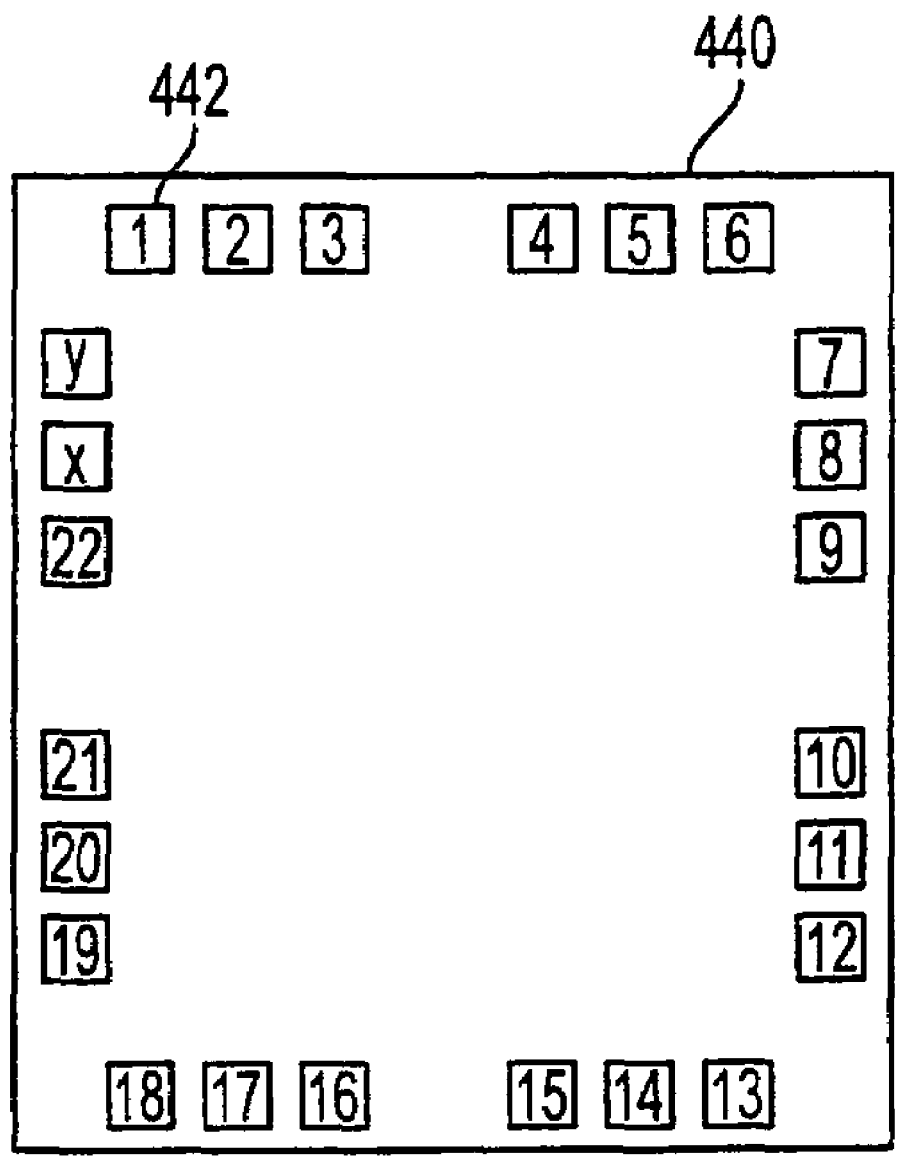

In a more preferred embodiment, the slide 70 includes positive and negative controls in the regions 440 which are those which are in contact with the hybridization fluid in each of the 8 wells 410. Using microarray technology which has become quite popular recently, nucleic acids which are complementary to the probes being used to paint the chromosomes are coated and immobilized onto the slide 70, preferably prior to placing cells upon the slides 70. This may best be performed under industrial conditions and the slides 70 can be sold with the controls built in. It is preferred that 24 controls 442 are placed onto each slide 70 at all 8 regions which are to be in contact with hybridization buffer. One example of an array is shown in FIG. 6E in which all 24 nucleic acids are arrayed around the edges of each region 440 which will contact each of the 8 wells 410. If for example, a first region 440 is one which will contact a well 410 containing probes for chromosomes 1, 2 and 3, then the control nucleic acids for these chromosomes should light up after staining (each showing only a single color) while the remaining 21 controls should not hybridize and should not fluoresce. In this manner there are both positive and negative controls and labels for each of the 8 wells 410.

One of skill in the art recognizes that other similarly designed trays can be utilized. There is no need for an 8 well tray. For example, if 4 differently colored fluorescent probes are to be used, the same results could be obtained with a 6 well tray. Furthermore, this invention is not limited to the analysis of human chromosomes. Chromosomes from any other organism can be similarly examined and the number of wells on the tray is a matter of personal choice, often determined by the number of chromosomes or probes to be examined. One of skill in the art also recognizes that trays can be designed to hold more than a single slide such that multiple cell samples can be assayed at once, with the multiple slides being handled together more easily than several separate slides.

Example 9

Coverslip with Concave Wells

Figure 7C:
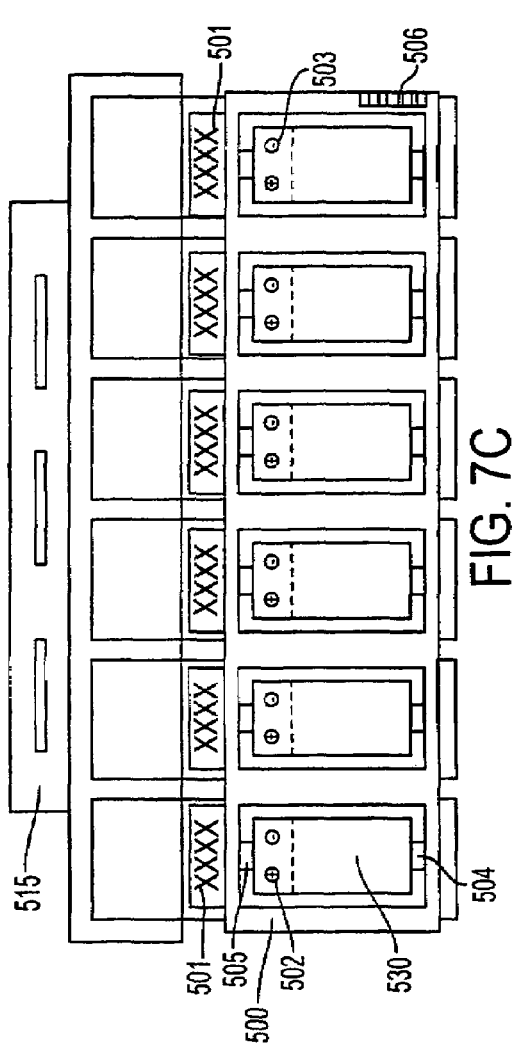

Rather than using a method of simply dropping reagents onto biological samples mounted onto a slide or placing the slide onto a tray with wells which are filled with reagents, a slide or series of attached slides can be covered with a coverslip wherein the coverslip is concave thereby comprising one or more wells. This is illustrated in FIGS. 7A-E which illustrates samples on six slides being analyzed simultaneously. FIG. 7A shows slides 510 with mounted biological samples 520 held in slideholder 515. FIG. 7B illustrates a coverslip 500 which is to fit over the slides 510 of FIG. 7A. Insert 540 discussed below may include writing 501 which can display information. Regions 502 and 503 are positive and negative controls, respectively. Controls 502 and 503 can be, e.g., protein, nucleic acid or a cell line, depending upon the specific type of assay being performed. Channels to allow the inlet of liquids and the outlet of air are shown as 504 and 505. The well 530 is also illustrated. The coverslips 500 can also be labeled with a barcode, shown in FIG. 7B as 506 or can have text written on them.

FIG. 7C shows coverslip 500 placed onto slides 510. The coverslip 500 is placed onto the slide 510 with mounted biological sample 520 and is affixed to the slide 510 at the top portion of the coverslip 500. The slide 510 and coverslip 500 are then dipped into water, buffer or reagent. Capillary action will cause the liquid to rise into the well 530 of the coverslip 500. Surface tension will hold the coverslip 500 securely to the slide 510. This results in an enclosed system with a known volume and concentration of reagent.

Figure 7D:
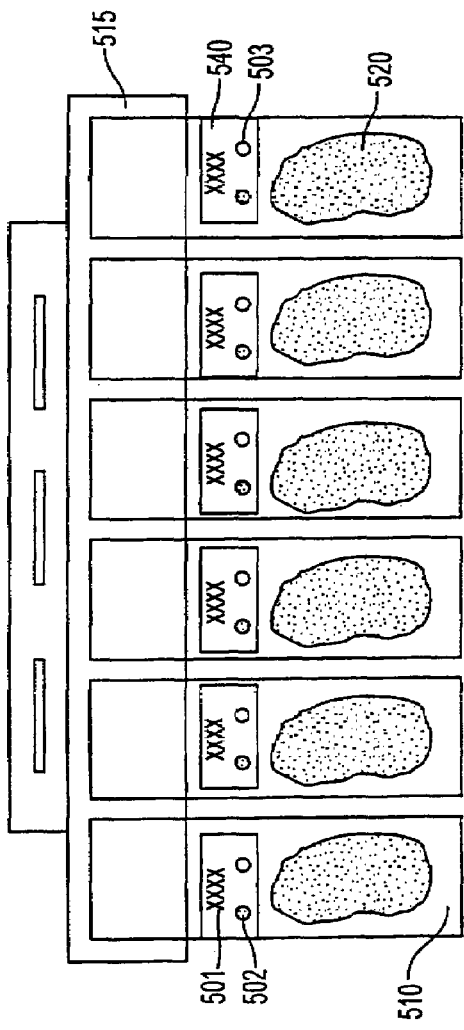

FIG. 7D illustrates the results after reaction has occurred and the coverslip 500 has been removed. The biological samples 520 and the positive controls 502 are shown as being stained.

In a preferred aspect of the invention, the coverslip 500 has had reagent or reagents predried onto it. When a coverslip 500 with predried reagent is placed onto a microscope slide 510 with biological sample 520; the slide 510 and coverslip 500 are merely dipped into water or buffer thereby causing liquid to fill the well 530 of the coverslip 500 and dissolve the dried reagent. The slide 510 and coverslip 500 are then removed from the water or buffer and the reaction is allowed to proceed. Known amounts of reagent or reagents are predried thereby resulting in precisely known amounts of reagents within the well 530 and thereby in contact with the biological sample 520. The volume of the well 530 is also known thereby resulting in a known concentration of reagent.

In another preferred aspect of the invention, the coverslip 500 is attached to the slide 510 by gluing an insert 540, e.g., glass or plastic, to the slide 510 using a glue which is resistant to both organic and aqueous liquids. This is illustrated in FIGS. 7E-H for a single slide and coverslip for a single slide. Coverslip 500 including well 530 with channels 504 and 505 is placed onto insert 540. FIG. 7F illustrates insert 540 which includes positive 502 and negative 503 controls, writing 501 to identify the insert 540, and a region of water-soluble glue 542. The upper portion of the coverslip 500 is thereby glued to the insert 540 using a glue which is water soluble. Controls 502 and 503 are located such that they are within the well 530 region of the coverslip 500. The back side of insert 540 is placed against and affixed to slide 510 by means such as a glue which is resistant to both organic and aqueous solutions. The slide 510 plus coverslip 500 is dipped into buffer and removed and the reaction is allowed to proceed. The slide 510 plus coverslip 500 can then be processed by placing into tanks of reagents or wash solution. Aqueous solutions will cause the water soluble glue to dissolve thereby releasing the coverslip 500 but not the insert 540. The coverslip 500 is easily removed at this point. Insert 540 remains on slide 510 as a control and label.

In a further aspect of the invention, the slides 510 have control samples 502 and 503 affixed to them. The controls 502 and 503 can either be spotted onto the slides 510, be on pieces of paper or stamps which are glued to the slide 510, or they can be on the insert 540. These control samples, which can be positive controls, negative controls, or both (affixed as separate spots) are used to determine that the reactions have worked properly. If the controls 502 and 503 are affixed to the insert 540, they are affixed at a point which will not be covered by glue and which overlaps the well 530 of the coverslip 500 so that the control samples 502 and 503 are in contact with buffer and reagents.

The inserts 540 can be premade with controls 502 and 503 and then used when needed. These inserts 540 can further include writing to indicate the names of the controls 502 and 503 and whether they are positive or negative.

The coverslips 500 can also be labeled and may include bar codes 560 for easy or automated reading. Coverslips 500 with predried reagents are easily stored and are ready for use making their use very convenient. Use of coverslips 500 with predried reagents further means that pipetting of small, accurate amounts of reagents is not required at the time of analysis thereby allowing faster analysis of the biological samples.

Example 10

Automated Method for Processing Biological Samples on Slides

A method similar to that of Example 9 can be automated such as by using a reaction chamber as illustrated in FIGS. 5A-B. One difference is that the coverslip to be used in the automated procedure need not include a well but can be flat. FIGS. 8A-D illustrate the method. Slides 600 with biological samples 610 are placed into slideholder 620. Coverslip 630 includes region 640 which can contain written information. Control samples 650 and 660 can be included on the coverslip 630. The coverslip 630 can also include a barcode 670 or can include text written on it. Slides 600 with biological samples 610 are placed into a reaction chamber. e.g., as shown in FIGS. 5A-B, for processing with organic reagents to deparaffinize the samples 610. In a preferred embodiment, several slides 600 are placed into a single slideholder 620 as shown in FIG. 8A. After deparaffinizing the samples 610 and washing, reagents can be added to the reaction chamber. In a preferred embodiment, coverslip 630 is placed into the reaction chamber together with slides 600. This is illustrated in FIG. 8C which shows both the coverslip 630 and slideholder 620 with slides 600, although the reaction chamber is not illustrated. Coverslip 630 preferably has reagent predried onto it, preferably in region 680. Addition of water or buffer dissolves the reagent which then reacts with biological sample 610 as well as with control samples 650 and 660. Following reaction wash solutions can be passed through the reaction chamber. Upon completion of the wash, the coverslip 630 can be pushed against slides 600 which are removed together from the reaction chamber and are kept together. i.e., the coverslip 630 acts as a permanent coverslip unlike the coverslip 500 in Example 9. FIG. 8D shows the coverslip 630 mounted onto slides 600 with the biological samples 610 and positive controls 650 being positive.

The preferred method of predrying known amounts of reagent onto the coverslip 630 allows for very quick and easy use in a clinical laboratory. The reagents need not be measured or pipetted. Instead a coverslip 630 is simply dropped into a reaction chamber together with the slide 600 with biological sample 610 and the reaction is allowed to proceed. Furthermore, the coverslip 630 can include positive and negative controls prespotted on to it thereby allowing for simple analysis of whether the reaction has worked properly.

Use of the above methods allows one to obtain results of a whole panel of markers in as little as 15-30 minutes. Thus the results can be obtained while the patient is still in the operating room. The pathologist and surgeon can decide immediately whether to perform more surgery or if chemotherapy or radiation treatment is necessary. This can allow the surgeon to proceed immediately rather than having to perform more surgery at a later date. If the currently sold automated system were used instead of the methods of the instant invention, it would take longer to receive results, partially because the currently sold automated system does not assay one patient at a time but rather many samples are loaded into the automated instrument at one time and it is necessary to wait while they are all loaded and then processed. The currently sold automated system drops reagents on top of slides and the biological sample is not always completely covered, whereas the present method of placing a biological sample on top of a well filled with reagents ensures that the whole sample is in contact with reagent.

The above Examples are only exemplary and not meant to be limiting of the techniques which may be performed using the apparatus which is defined by the present invention. The invention is applicable to, but not limited to, immunohistochemistry, in situ hybridization, in situ PCR, and fluorescent in situ hybridization (FISH). The stated measurements are also exemplary and not meant to be limiting as it will be obvious to one of skill in the art that the exact measurements are not critical and can be varied to still yield successful results. Those skilled in the art will readily perceive other applications for the present invention.

LIST OF REFERENCES

Brigati D J, et al. (1988). *J. Histotechnology* 11:165-183.
Compton J (1991). *Nature* 350:91-92.
Fahy E, et al. (1991). *PCR Methods Appl.* 1:25-33.
Innis M A, et al. (1990). *PCR Protocols: A Guide to Methods and Applications* (Academic Press San Diego).
Nuovo G J (1994). *J Histotechnology* 17:235-242.
Spargo C A, et al. (1996). *Mol. Cell. Probes* 10:247-256.
Walker G T, et al. (1992). *Nucl. Acids Res.* 20:1691-1696.
Wu D Y and Wallace R B (1989). *Genomics* 4:560-569.
U.S. Pat. No. 4,683,195
U.S. Pat. No. 4,683,202
U.S. Pat. No. 5,270,184
U.S. Pat. No. 5,409,818
U.S. Pat. No. 5,455,166
U.S. Pat. No. 5,958,341

What is claimed is:

1. A slide comprising a microscope slide having a control region apart from a biological sample region and a membrane mounted on the control region of said microscope slide, having at least one control placed on the membrane wherein said membrane comprises said control on a first face of said membrane and a substance on a second face of said membrane wherein said substance causes said membrane to adhere to said microscope slide when contacted with said microscope slide.

2. The slide of claim 1, wherein said substance is glue.

3. The slide of claim 1, wherein said control is selected from the group consisting of: an external control, a positive control, and a negative control.

4. The slide of claim 1, wherein said control is selected from the group consisting of antigens, peptides, proteins, nucleic acids and cells.

5. The slide of claim 2 wherein said glue is resistant to xylene and alcohol.

6. The slide of claim 1, wherein said membrane is selected from the group consisting of: nitrocellulose, plastic, glass, and nylon.

7. The slide of claim 1, wherein said membrane is transparent.

8. The slide of claim 1, wherein said membrane comprises a plurality of said controls.

9. A method of assaying a biological sample on said slide of claim 1, comprising one or more of said controls placed on said membrane of said control region and the biological sample placed on said biological sample region and assaying simultaneously said one or more controls and said biological sample.

10. The method of claim 9, wherein said slide is placed on a well of a multiwell tray containing one or more reagents which react with said biological sample.

11. A kit comprising said slide of claim 1 in combination with a multiwell tray.

12. The kit of claim 11, wherein said multiwell tray comprises predried reagents.

13. The kit of claim 11, wherein a reagent added to a well of said multiwell tray reacts with said control on said membrane.

* * * * *